US012422441B2

(12) United States Patent
Lieberman et al.

(10) Patent No.: US 12,422,441 B2
(45) Date of Patent: Sep. 23, 2025

(54) ANTIBODIES THAT BIND TO NATIVELY FOLDED MYOCILIN

(71) Applicants: Georgia Tech Research Corporation, Atlanta, GA (US); Board of Regents, The University of Texas System, Austin, TX (US)

(72) Inventors: Raquel L. Lieberman, Atlanta, GA (US); Shannon E. Hill, Lutz, FL (US); Athena Patterson-Orazem, Gaithersburg, MD (US); Jennifer A. Maynard, Austin, TX (US); Ahlam Qerqez, Austin, TX (US); Laura Azouz Yuan, Austin, TX (US)

(73) Assignee: Georgia Tech Research Corporation, Atlanta, GA (US)

( * ) Notice: Subject to any disclaimer, the term of this patent is extended or adjusted under 35 U.S.C. 154(b) by 1009 days.

(21) Appl. No.: 17/311,547

(22) PCT Filed: Dec. 9, 2019

(86) PCT No.: PCT/US2019/065196
§ 371 (c)(1),
(2) Date: Jun. 7, 2021

(87) PCT Pub. No.: WO2020/118293
PCT Pub. Date: Jun. 11, 2020

(65) Prior Publication Data
US 2022/0026445 A1 Jan. 27, 2022

Related U.S. Application Data

(60) Provisional application No. 62/776,799, filed on Dec. 7, 2018.

(51) Int. Cl.
*G01N 33/68* (2006.01)
*C07K 16/18* (2006.01)

(52) U.S. Cl.
CPC ......... *G01N 33/6893* (2013.01); *C07K 16/18* (2013.01); *C07K 2317/33* (2013.01); *C07K 2317/34* (2013.01); *C07K 2317/524* (2013.01); *C07K 2317/526* (2013.01); *G01N 2800/168* (2013.01)

(58) Field of Classification Search
CPC ................ C07K 16/18; C07K 2317/33; C07K 2317/34; C07K 2317/524; C07K 2317/526; G01N 2400/00; G01N 2800/168; G01N 33/6893
See application file for complete search history.

(56) References Cited

U.S. PATENT DOCUMENTS

| | | | |
|---|---|---|---|
| 4,444,887 A | 4/1984 | Hoffmann | |
| 4,716,111 A | 12/1987 | Osband et al. | |
| 4,816,397 A | 3/1989 | Boss et al. | |
| 4,816,567 A | 3/1989 | Cabilly et al. | |
| 5,225,539 A | 7/1993 | Winter | |
| 5,413,923 A | 5/1995 | Kucherlapati et al. | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,569,825 A | 10/1996 | Lonberg et al. | |
| 5,585,089 A | 12/1996 | Queen et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,693,761 A | 12/1997 | Queen et al. | |
| 5,693,762 A | 12/1997 | Queen et al. | |
| 5,766,886 A | 6/1998 | Studnicka et al. | |
| 5,807,715 A | 9/1998 | Morrison et al. | |
| 5,814,318 A | 9/1998 | Lonberg et al. | |
| 5,916,771 A | 6/1999 | Hori et al. | |
| 5,939,598 A | 8/1999 | Kucherlapati et al. | |
| 6,005,079 A | 12/1999 | Casterman et al. | |
| 6,180,370 B1 | 1/2001 | Queen et al. | |
| 6,311,415 B1 | 11/2001 | Lind | |
| 6,331,415 B1 | 12/2001 | Cabilly et al. | |
| 6,350,861 B1 | 2/2002 | Co et al. | |
| 6,407,213 B1 | 6/2002 | Carter et al. | |
| 8,846,870 B2 * | 9/2014 | Kawai | G01N 33/57423 530/387.9 |

(Continued)

FOREIGN PATENT DOCUMENTS

| | | |
|---|---|---|
| EP | 0592106 A1 | 4/1994 |
| EP | 0239400 B1 | 8/1994 |

(Continued)

OTHER PUBLICATIONS

Brown et al., "Tolerance of single, but not multiple, amino acid replacements in antibody VH CDR 2: a means of minimizing B cell wastage from somatic hypermutation?", J. Immunol., 1996 vol. 156, No. 9, pp. 3285-3291.*
Gabrielli et al., "Antibody Complementarity-Determining Regions (CDRs): A Bridge between Adaptive and Innate Immunity," PLoS One, 2009, vol. 4, issue 12, e8187 pp. 1-12.*
Almagro et al., "Humanization of Antibodies", Frontiers in Bioscience, 2008, vol. 13, pp. 1619-1633.*
Goel et al., "Plasticity within the Antigen Combining Site May Manifest as Molecular Mimicry in the Humoral Immune Response", J. Immunol., 2004, vol. 173, No. 12, pp. 7358-7367.*
Edwards et al., "The remarkable flexibility of the human antibody repertoire; isolation of over one thousand different antibodies to a single protein, BLyS," J. Mol. Biol., 2003, vol. 334, pp. 103-118.*

(Continued)

*Primary Examiner* — Galina M. Yakovleva
(74) *Attorney, Agent, or Firm* — Troutman Pepper Locke LLP; Ryan A. Schneider; Nicholas H. Doss

(57) ABSTRACT

Myocilin-binding agents including antibodies and antigen binding fragments thereof and fusion proteins that immunospecifically bind the coiled-coil domain of myocilin but do not bind to misfolded myocilin are provided herein. The disclosed antibodies and antigen binding fragments and fusion proteins are useful for the detection and extraction of natively folded myocilin from a sample.

18 Claims, 10 Drawing Sheets

Specification includes a Sequence Listing.

(56) References Cited

U.S. PATENT DOCUMENTS

| | | | |
|---|---|---|---|
| 9,732,156 B2* | 8/2017 | Adamkewicz | A61P 21/00 |
| 2003/0229208 A1 | 12/2003 | Queen et al. | |
| 2004/0049014 A1 | 3/2004 | Queen et al. | |
| 2005/0037000 A1 | 2/2005 | Stavenhagen et al. | |
| 2005/0064514 A1 | 3/2005 | Stavenhagen et al. | |
| 2009/0298839 A1 | 12/2009 | McCarty et al. | |
| 2010/0260783 A1 | 10/2010 | Matsubara et al. | |
| 2011/0262929 A1 | 10/2011 | Kawai et al. | |

FOREIGN PATENT DOCUMENTS

| | | | |
|---|---|---|---|
| EP | 0519596 B1 | 2/2005 | |
| GB | 2188638 A | 10/1987 | |
| GB | 2209757 A | 5/1989 | |
| WO | 91/09967 A1 | 7/1991 | |
| WO | 91/10741 A1 | 7/1991 | |
| WO | 93/17105 A1 | 9/1993 | |
| WO | 94/04678 A1 | 3/1994 | |
| WO | 94/25591 A1 | 11/1994 | |
| WO | 96/33735 A1 | 10/1996 | |
| WO | 96/34096 A1 | 10/1996 | |
| WO | 98/16654 A1 | 4/1998 | |
| WO | 98/24893 A2 | 6/1998 | |
| WO | 98/32850 A1 | 7/1998 | |
| WO | 98/46645 A2 | 10/1998 | |
| WO | 98/50433 A2 | 11/1998 | |
| WO | 02/82969 A2 | 10/2002 | |
| WO | 2020/118293 A2 | 6/2020 | |

OTHER PUBLICATIONS

Lloyd et al., "Modelling the human immune response: performance of a 10e11 human antibody repertoire against a broad panel of therapeutically relevant antigens," Protein Engineering, Design and Selection, 2009, vol. 22, issue 3, pp. 159-168.*
Vajdos et al., "Comprehensive functional maps of the antigen-binding site of an anti-ErbB2 antibody obtained with shotgun scanning mutagenesis," J. Mol. Biol., 2002, vol. 320, No. 2, pp. 415-428.*
Baca, M., et al., "Antibody Humanization Using Monovalent Phage Display", J. Biol. Chem., 272(6): 10678-10684 (1997).
Caldas, C., et al., "Design and synthesis of germline-based hemi-humanized single-chain Fv against the CD18 surface antigen", Protein Eng., 13(5): 353-360 (2000).
Changula, et al., "Mapping of conserved and species-specific antibody epitopes on the Ebola virus nucleoprotein", Virus Res, 176: 83-90 (2013).
Chothia, et al., "Canonical structures for the hypervariable regions of immunoglobulins", J. Mol. Biol., 196: 901-917 (1987).
Chothia, et al., "Structural Determinants in the Sequences of Immunoglobulin Variable Domain", J. Mol. Biol., 278: 457-479 (1998).
Couto, J.R, et al., "Designing Human Consensus Antibodies with Minimal Positional Templates", Cancer Res., 55(23 Supp): 5973s-5977s (1995).
Couto, J.R., "Anti-BA46 Monoclonal Antibody Mc3: Humanization Using a Novel Positional Consensus and in Vivo and in Vitro Characterization", et al., Cancer Res., 55: 1717-1722 (1995).
Eshed, Y., et al., "Secreted gliomedin is a perinodal matrix component of peripheral nerves", Journal of Cell Biology, 177: 551-562 (2007).
Ezzat, M.K., et al., "Characterization of monoclonal antibodies againstt the glaucoma-associated protein myocilin", Experimental Eye Research, 87(4): 376-384 (2008).
Fautsch, et al., "Characterization of Myocilin-Myocilin Interactions", Investigative Ophthalmology & Visual Science, 42: 2324-2331 (2001).
Fautsch, et al., "In vitro and in vivo characterization of disulfide bond use in myocilin complex formation", Molecular Vision, 10: 417-425 (2004).

Fingert, J.H., et al., "Myocilin Glaucoma", Surv Ophthalmol, 47: 547-561 (2002).
Furlong, S.T., et al., "Synthesis and physical characterization of a P1 arginine combinatorial library, and its application to the determination of the substrate specificity of serine peptidases", Bioorg Med Chem, 10: 3637-3647 (2002).
Gillies, S.D., et al., "High-level expression of chimeric antibodies using adapted cDNA variable region cassettes", J. Immunol. Methods, 125: 191-202 (1989).
Gobeil, S., et al., "Intracellular Sequestration of Hetero-oligomers Formed by Wild-Type and Glaucoma-Causing Myocilin Mutants", Investigative Ophthalmology & Visual Science, 45(10): 3560-3567 (2004).
Goldwich, A., et al.,"Perfusion with the Olfactomedin Domain of Myocilin Does Not Affect Outflow Facility", Invest Opthamol Vis Sci, 44: 1952-1961 (2003).
Goyal, et al., "Evaluation of Oxidative Stress Markers in Aqueous Humor of Primary Open Angle Glaucoma and Primary Angle Closure Glaucoma Patients", Curr Eye Res, 39: 823-829 (2014).
Greenspan, N.S., et al., "Idiotypes: Structure And Immunogenicity", FASEB J., 7: 437-444 (1989).
Hill, S.E., et al., "Structure and Misfolding of the Flexible Tripartite Coiled-Coil Domain of Glaucoma-Associated Myocilin", Structure, 25(11): 1697-1707 (2017).
Hill, S.E., et al., "The Glaucoma-Associated Olfactomedin Domain of Myocilin Forms Polymorphic Fibrils That Are Constrained by Partial Unfolding and Peptide Sequence", Journal of Molecular Biology, 426(4): 921-935 (2014).
International Search Report received for PCT/US2019/065196, mailed on Jun. 29, 2020 (7 pages).
Ionescu, R.M., et al., "Contribution of Variable Domains to the Stability of Humanized IgG1 Monoclonal Antibodies", J Pharm Sci, 97: 1414-1426 (2008).
Jones, P.T., et al., "Replacing the complementarity-determining regions in a human antibody with those from a mouse", Nature, 321: 522-525 (1986).
Jonhson, T.V., et al., "Rodent models of glaucoma", Brain Res Bull, 81: 349-358 (2010).
Keller, K.E., et al., "Consensus recommendations for trabecular meshwork cell isolation, characterization and culture", Exp Eye Res, 171: 164-173 (2018).
Krebber, A., et al., "Reliable cloning of functional antibody variable domains from hybridomas and spleen cell repertoires employing a reengineered phage display system", J Immunol Methods, 201: 35-55 (1997).
Lonberg, N., et al., "Human Antibodies from Transgenic Mice", Int. Rev. Immunol., 13: 65-93 (1995).
Maertens, B., et al., "Cleavage and Oligomerization of Gliomedin, a Transmembrane Collagen Required for Node of Ranvier Formation", Journal of Biological Chemistry, 282(14): 10647-10659 (2007).
Majsterek, I., et al., "Evaluation of oxidative stress markers in pathogenesis of primaryopen-angle glaucoma", Exp Mol Pathol, 90: 231-237 (2011).
Mathiowitz, et al., "Novel Microcapsules for Delivery Systems", Reactive Polymers, 6: 275-283 (1987).
Mathiowitz, et al., "Polyanhydride microspheres as drug carriers I. Hot-melt microencapsulation", Controlled Release, 5: 13-22 (1987).
Mathiowitz, et al., "Polyanhydride microspheres as drug carriers. II. Microencapsulation by solvent removal", J. Appl. Polymer Sci., 35: 755-774 (1988).
Morea, V., et al., "Antibody Modeling: Implications for Engineering and Design", Methods, 20: 267-279 (2000).
Morrison, S.L., "Transfectomas provide novel chimeric antibodies", Science, 229: 1202-1207 (1985).
Mueller, J.P., et al., "Humanized porcine VCAM-specific monoclonal antibodies with chimeric IgG2/G4 constant regions block human leukocyte binding to porcine endothelial cells", Mol. Immun., 34(6): 441-452 (1997).
Muyldermans, S., et al., "Recognition of antigens by single-domain antibody fragments: the superfluous luxury of paired domains", Trends Biochem. Sci., 26: 230-235 (2001).
Nisonoff, A., "Idiotypes: Concepts And Applications", J. Immunol., 147(8): 2429-2438 (1991).

(56) References Cited

OTHER PUBLICATIONS

Nuttall, S.D., et al., "Immunoglobulin VH Domains and Beyond: Design and Selection of Single-Domain Binding and Targeting Reagents", Curr. Pharm. Biotech., 1: 253-263 (2000).
Oi, V.T., et al., "Chimeric antibodies", BioTechniques, 4: 214-221 (1986).
Orwig, S.D., et al., "Amyloid Fibril Formation by the Glaucoma-AssociatedOlfactomedin Domain of Myocilin", Journal of Molecular Biology, 421: 242-255 (2012).
Padlan, E.A., "A possible procedure for reducing the immunogenicity of antibody variable domains while preserving their ligand-binding properties", Molecular Immunology, 28(4/5): 489-498 (1991).
Patterson-Orazem, A.C., et al., "Epitope mapping of commercial antibodies that detect myocilin", Experimental Eye Research, 173: 109-112 (2018).
Pedersen, J.T., et al., "Comparison of Surface Accessible Residues in Human and Murine Immunoglobulin Fv Domains: Implication for Humanization of Murine Antibodies", J. Mol. Biol., 235: 959-973 (1994).
Pluckthun, The Pharmacology of Monoclonal Antibodies, 113: 269-315 (1994).
Polansky, J.R., et al., "Cellular Pharmacology and Molecular Biology of the Trabecular Meshwork Inducible Glucocorticoid Response Gene Productm", Ophthalmologica, 211: 126-139 (1997).
Presta, L.G., "Antibody Engineering", Curr. Op. Struct. Biol., 2: 593-596 (1992).
Presta, L.G., "Molecular engineering and design of therapeutic antibodies", Cur. Opin. Immun., 20: 460-470 (2008).
Reichmann, L., et al., "Reshaping human antibodies for therapy", Nature, 332: 323-329 (1988).
Roguska, M.A., et al., "A comparison of two murine monoclonal antibodies humanized by CDR-grafting and variable domain resurfacing ", Protein Eng., 9: 895-904 (1996).
Roguska, M.A., et al., "Humanization of murine monoclonal antibodies through variable domain resurfacing", Proc. Natl. Acad. Sci. USA, 91: 969-973 (1994).
Sanchez-Sanchez, F., et al., "Characterization of the Intracellular Proteolytic Cleavage of Myocilin and Identification of Calpain Il as a Myocilin-processing Protease", J Biol Chem, 282: 27810-27824 (2007).
Sandhu, J.S., "A rapid procedure for the humanization of monoclonal antibodies", Gene, 150: 409-410 (1994).
Schilling, O., et al., "Factor Xa subsite mapping by proteome-derived peptide libraries improved using WebPICS, a resource for proteomic identification of cleavage sites", Biol Chem, 392: 1031-1037 (2011).
Schneider, C.A., et al., "NIH Image to ImageJ: 25 years of image analysis", Nat Methods, 9: 671-675 (2012).
Shepard, A.R., et al., "Characterization of rabbit myocilin: Implications for human myocilin glycosylation and signal peptide usage", BMC Genetics, 4: 1-10 (2003).
Silva, J.P., et al., "Functional Cross-interaction of the Fragments Produced by the Cleavage of Distinct Adhesion G-protein-coupled Receptors", Journal of Biological Chemistry, 284: 6495-6506 (2009).
Smith, K., et al., "Rapid generation of fully human monoclonal antibodies specific to a vaccinating antigen", Nat Protoc, 4: 372-384 (2009).
Stamer, W.D., et al., "Coiled-coil targeting of myocilin to intracellular membranes", Experimental Eye Research 83: 1386-1395 (2006).
Studnicka, G.M., et al., "Human-engineered monoclonal antibodies retain full specific binding activity by preserving non-CDR complementarity-modulating residues", Protein Engineering, 7: 805-814 (1994).
Swann, P.G., et al., "Considerations for the development of therapeutic monoclonal antibodies", Cur. Opin. Immun., 20: 493-499 (2008).
Tamm, E.R., et al., "Modulation of Myocilin/TIGR Expression in Human Trabecular Meshwork", Invest Ophthalmol Vis Sci, 40: 2577-2582 (1999).
Tan, P., et al., "'Superhumanized' Antibodies: Reduction of Immunogenic Potential by Complementarity-Determining Region Grafting with Human Germline Sequences: Application to an Anti-CD28", J. Immunol., 169: 1119-1125 (2002).
Westernberg, L., et al., "T-cell epitope conservation across allergen species is a major determinant of immunogenicity", J Allergy Clin Immunol, 138: 571-578 (2016).
Reichmann and Muyldermans, "Single domain antibodies: comparison of camel VH and camelised human VH domains," Journal of Immunological Methods 231 (1999) pp. 25-38.
Patterson-Orazem et al., "Recombinant antibodies recognize conformation-dependent epitopes of the leucine zipper of misfolding-prone myocilin." J Biol Chem. Sep. 2021;297(3):101067.

* cited by examiner

| | | | X | X | X | X | | X | | | SEQ ID NO: |
|---|---|---|---|---|---|---|---|---|---|---|---|
| WT | Q | Q | Y | N | S | Y | P | Y | T | | 11 |
| 1S5 | Q | Q | Y | M | Y | L | P | I | T | | 14 |
| 2H2 | Q | Q | Y | N | S | Y | P | Y | T | | 11 |
| 2S2 | Q | Q | Y | F | A | L | P | I | T | | 15 |
| 4L4 | Q | Q | Y | D | V | V | P | R | T | | 16 |
| 4L7 | Q | Q | Y | A | F | F | P | L | T | | 17 |

FIG. 5A

Variable positions (stacked above): position 4: Y/A/S; position 8: Y/A/D/S/*; position 10: Y/A/D/S/*; position 11: Y/D/S/H; position 12: Y/R/S/N/C/W/*; position 14: K

| | | | | | | | | | | | | | | | | | | SEQ ID NO: |
|---|---|---|---|---|---|---|---|---|---|---|---|---|---|---|---|---|---|---|
| WT | W | I | D | P | E | N | G | D | T | E | Y | A | P | K | F | Q | G | 13 |
| 1S5 | W | I | D | P | E | N | G | D | T | E | Y | A | P | K | F | Q | G | 13 |
| 2H2 | W | I | D | P | A | N | G | S | T | Y | Y | S | D | K | F | Q | G | 18 |
| 2S2 | W | I | D | P | E | N | G | D | T | E | Y | A | P | K | F | Q | G | 13 |
| 4L4 | W | I | D | P | E | N | G | D | T | E | Y | A | P | K | F | Q | G | 13 |
| 4L7 | W | I | D | P | E | N | G | D | T | E | Y | A | P | K | F | Q | G | 13 |

FIG. 5B

|  |  |  | X | X | X | X |  | X |  | SEQ ID NO: |
|---|---|---|---|---|---|---|---|---|---|---|
| WT | Q | Q | Y | N | S | Y | P | Y | T | 11 |
| 96w-out4-L1 | Q | Q | Y | K | W | L | P | L | T | 19 |
| 96w-out4-L2 | Q | Q | Y | N | E | L | P | I | T | 20 |
| 96w-out4-L3 | Q | Q | Y | D | F | F | P | L | T | 21 |
| 96w-out4-L4 | Q | Q | Y | D | V | V | P | R | T | 16 |
| 96w-out4-L5 | Q | Q | Y | T | F | L | P | I | T | 22 |
| 96w-out4-L6 | Q | Q | Y | S | A | L | P | L | T | 23 |
| 96w-out4-L7 | Q | Q | Y | A | F | F | P | L | T | 17 |
| 96w-out4-L8 | Q | Q | Y | D | A | V | P | L | T | 24 |
| 96w-out4-L9 | Q | Q | Y | S | V | L | P | I | T | 25 |
| 96w-out4-L11 | Q | Q | Y | D | V | L | P | L | T | 26 |
| 96w-out4-L12 | Q | Q | Y | E | F | F | P | R | T | 27 |
| 96w-out1-S1 | Q | Q | Y | F | L | L | P | I | T | 28 |
| 96w-out1-S2 | Q | Q | Y | Q | E | V | P | R | T | 29 |
| 96w-out1-S3 | Q | Q | Y | A | S | V | P | L | T | 30 |
| 96w-out1-S4 | Q | Q | Y | G | Y | L | P | L | T | 31 |
| 96w-out1-S5 | Q | Q | Y | M | Y | L | P | I | T | 14 |
| 96w-out1-S6 | Q | Q | Y | A | F | L | P | V | T | 32 |
| 96w-out1-S7 | Q | Q | Y | D | R | V | P | L | T | 33 |
| 96w-out1-S8 | Q | Q | Y | D | R | V | P | L | T | 33 |
| 96w-out1-S9 | Q | Q | Y | A | F | L | P | L | T | 34 |
| 96w-out1-S10 | Q | Q | Y | R | F | L | P | I | T | 35 |
| 96w-out1-S11 | Q | Q | Y | N | S | L | P | L | T | 36 |
| 96w-out1-S12 | Q | Q | Y | M | Y | L | P | L | T | 37 |
| 96w-out2-S2 | Q | Q | Y | F | A | L | P | I | T | 15 |
| 96w-out2-S3 | Q | Q | Y | F | A | L | P | I | T | 15 |
| 96w-out2-S5 | Q | Q | Y | D | V | L | P | L | T | 26 |
| 96w-out2-S6 | Q | Q | Y | A | S | L | P | I | T | 38 |
| 96w-out2-S7 | Q | Q | Y | D | V | L | P | I | T | 39 |
| 96w-out2-S8 | Q | Q | Y | A | F | L | P | I | T | 40 |
| 96w-out2-S9 | Q | Q | Y | M | F | L | P | L | T | 41 |
| 96w-out2-S11 | Q | Q | Y | F | A | L | P | I | T | 15 |
| 96w-out2-S12 | Q | Q | Y | F | A | L | P | I | T | 15 |
| Preferred residues |  |  | Y |  |  | Hydrophobic | | Hydrophobic | | |

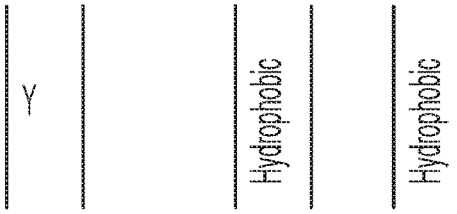

FIG. 5C

```
                                        Y
                                        R
                    Y           Y       S
                    A           A       N
              Y     D     Y     D       C
              A     S     D     S       W
              S     *     S     H       *           K
WT   W I D P E N G  D  T  E  Y  A  P    K    F Q G    SEQ ID NO:
                                                          13
─────────────────────────────────────────────────────────────
1S5  W I D P D D G  S  T  Y  Y  S  P    N    F K G        42
2H2  W I D P A N G  S  T  Y  Y  S  D    K    F Q G        18
2S2  W I D P S N G  D  T  Y  Y  A  H    R    F Q G        43
4L4  W I D P A N G  S  T  Y  Y  A  D    N    F K G        44
4L7  W I D P E D G  S  T  Y  Y  S  D    R    F K G        45
```

FIG. 5D

SEQUENCE LISTING

<160> NUMBER OF SEQ ID NOS: 45

<210> SEQ ID NO 1
<211> LENGTH: 504
<212> TYPE: PRT
<213> ORGANISM: Homo sapiens

<400> SEQUENCE: 1

Met Arg Phe Phe Cys Ala Arg Cys Cys Ser Phe Gly Pro Glu Met Pro
1               5                   10                  15

Ala Val Gln Leu Leu Leu Leu Ala Cys Leu Val Trp Asp Val Gly Ala
            20                  25                  30

Arg Thr Ala Gln Leu Arg Lys Ala Asn Asp Gln Ser Gly Arg Cys Gln
        35                  40                  45

Tyr Thr Phe Ser Val Ala Ser Pro Asn Glu Ser Ser Cys Pro Glu Gln
    50                  55                  60

Ser Gln Ala Met Ser Val Ile His Asn Leu Gln Arg Asp Ser Ser Thr
65                  70                  75                  80

Gln Arg Leu Asp Leu Glu Ala Thr Lys Ala Arg Leu Ser Ser Leu Glu
                85                  90                  95

Ser Leu Leu His Gln Leu Thr Leu Asp Gln Ala Ala Arg Pro Gln Glu
            100                 105                 110

Thr Gln Glu Gly Leu Gln Arg Glu Leu Gly Thr Leu Arg Arg Glu Arg
        115                 120                 125

Asp Gln Leu Glu Thr Gln Thr Arg Glu Leu Glu Thr Ala Tyr Ser Asn
    130                 135                 140

Leu Leu Arg Asp Lys Ser Val Leu Glu Glu Lys Lys Arg Leu Arg Gln
145                 150                 155                 160

Gln Glu Asn Glu Asn Leu Ala Arg Arg Leu Glu Ser Ser Ser Gln Glu
                165                 170                 175

Val Ala Arg Leu Arg Arg Gly Gln Cys Pro Gln Thr Arg Asp Thr Ala
            180                 185                 190

Arg Ala Val Pro Pro Gly Ser Arg Glu Val Ser Thr Trp Asn Leu Asp
        195                 200                 205

Thr Leu Ala Phe Gln Glu Leu Lys Ser Glu Leu Thr Glu Val Pro Ala
    210                 215                 220

Ser Arg Ile Leu Lys Glu Ser Pro Ser Gly Tyr Leu Arg Ser Gly Glu
225                 230                 235                 240

Gly Asp Thr Gly Cys Gly Glu Leu Val Trp Val Gly Glu Pro Leu Thr
                245                 250                 255

Leu Arg Thr Ala Glu Thr Ile Thr Gly Lys Tyr Gly Val Trp Met Arg
            260                 265                 270

Asp Pro Lys Pro Thr Tyr Pro Tyr Thr Gln Glu Thr Thr Trp Arg Ile
        275                 280                 285

Asp Thr Val Gly Thr Asp Val Arg Gln Val Phe Glu Tyr Asp Leu Ile
    290                 295                 300

Ser Gln Phe Met Gln Gly Tyr Pro Ser Lys Val His Ile Leu Pro Arg
305                 310                 315                 320

Pro Leu Glu Ser Thr Gly Ala Val Val Tyr Ser Gly Ser Leu Tyr Phe
                325                 330                 335

-continued

```
Gln Gly Ala Glu Ser Arg Thr Val Ile Arg Tyr Glu Leu Asn Thr Glu
                340                 345                 350

Thr Val Lys Ala Glu Lys Glu Ile Pro Gly Ala Gly Tyr His Gly Gln
            355                 360                 365

Phe Pro Tyr Ser Trp Gly Tyr Thr Asp Ile Asp Leu Ala Val Asp
        370                 375                 380

Glu Ala Gly Leu Trp Val Ile Tyr Ser Thr Asp Glu Ala Lys Gly Ala
385                 390                 395                 400

Ile Val Leu Ser Lys Leu Asn Pro Glu Asn Leu Glu Leu Glu Gln Thr
                405                 410                 415

Trp Glu Thr Asn Ile Arg Lys Gln Ser Val Ala Asn Ala Phe Ile Ile
            420                 425                 430

Cys Gly Thr Leu Tyr Thr Val Ser Ser Tyr Thr Ser Ala Asp Ala Thr
        435                 440                 445

Val Asn Phe Ala Tyr Asp Thr Gly Thr Gly Ile Ser Lys Thr Leu Thr
    450                 455                 460

Ile Pro Phe Lys Asn Arg Tyr Lys Tyr Ser Ser Met Ile Asp Tyr Asn
465                 470                 475                 480

Pro Leu Glu Lys Lys Leu Phe Ala Trp Asp Asn Leu Asn Met Val Thr
                485                 490                 495

Tyr Asp Ile Lys Leu Ser Lys Met
            500

<210> SEQ ID NO 2
<211> LENGTH: 194
<212> TYPE: PRT
<213> ORGANISM: Homo sapiens

<400> SEQUENCE: 2

Arg Thr Ala Gln Leu Arg Lys Ala Asn Asp Gln Ser Gly Arg Cys Gln
1               5                   10                  15

Tyr Thr Phe Ser Val Ala Ser Pro Asn Glu Ser Ser Cys Pro Glu Gln
            20                  25                  30

Ser Gln Ala Met Ser Val Ile His Asn Leu Gln Arg Asp Ser Ser Thr
        35                  40                  45

Gln Arg Leu Asp Leu Glu Ala Thr Lys Ala Arg Leu Ser Ser Leu Glu
    50                  55                  60

Ser Leu Leu His Gln Leu Thr Leu Asp Gln Ala Ala Arg Pro Gln Glu
65                  70                  75                  80

Thr Gln Glu Gly Leu Gln Arg Glu Leu Gly Thr Leu Arg Arg Glu Arg
                85                  90                  95

Asp Gln Leu Glu Thr Gln Thr Arg Glu Leu Glu Thr Ala Tyr Ser Asn
            100                 105                 110

Leu Leu Arg Asp Lys Ser Val Leu Glu Glu Glu Lys Lys Arg Leu Arg
        115                 120                 125

Gln Glu Asn Glu Asn Leu Ala Arg Arg Leu Glu Ser Ser Ser Gln Glu
    130                 135                 140

Val Ala Arg Leu Arg Arg Gly Gln Cys Pro Gln Thr Arg Asp Thr Ala
145                 150                 155                 160

Arg Ala Val Pro Pro Gly Ser Arg Glu Val Ser Thr Trp Asn Leu Asp
                165                 170                 175

Thr Leu Ala Phe Gln Glu Leu Lys Ser Glu Leu Thr Glu Val Pro Ala
            180                 185                 190

Ser Arg
```

<210> SEQ ID NO 3
<211> LENGTH: 111
<212> TYPE: PRT
<213> ORGANISM: Homo sapiens

<400> SEQUENCE: 3

Leu Gln Arg Asp Ser Ser Thr Gln Arg Leu Asp Leu Glu Ala Thr Lys
1               5                   10                  15

Ala Arg Leu Ser Ser Leu Glu Ser Leu Leu His Gln Leu Thr Leu Asp
            20                  25                  30

Gln Ala Ala Arg Pro Gln Glu Thr Gln Glu Gly Leu Gln Arg Glu Leu
        35                  40                  45

Gly Thr Leu Arg Arg Glu Arg Asp Gln Leu Glu Thr Gln Thr Arg Glu
    50                  55                  60

Leu Glu Thr Ala Tyr Ser Asn Leu Leu Arg Asp Lys Ser Val Leu Glu
65                  70                  75                  80

Glu Glu Lys Lys Arg Leu Arg Gln Glu Asn Glu Asn Leu Ala Arg Arg
                85                  90                  95

Leu Glu Ser Ser Ser Gln Glu Val Ala Arg Leu Arg Arg Gly Gln
            100                 105                 110

<210> SEQ ID NO 4
<211> LENGTH: 490
<212> TYPE: PRT
<213> ORGANISM: Mus musculus

<400> SEQUENCE: 4

Met Pro Ala Leu His Leu Leu Phe Leu Ala Cys Leu Val Trp Gly Met
1               5                   10                  15

Gly Ala Arg Thr Ala Gln Phe Arg Lys Ala Asn Asp Arg Ser Gly Arg
            20                  25                  30

Cys Gln Tyr Thr Phe Thr Val Ala Ser Pro Asn Glu Ser Ser Cys Pro
        35                  40                  45

Arg Glu Asp Gln Ala Met Ser Ala Ile Gln Asp Leu Gln Arg Asp Ser
    50                  55                  60

Ser Ile Gln His Ala Asp Leu Glu Ser Thr Lys Ala Arg Val Arg Ser
65                  70                  75                  80

Leu Glu Ser Leu Leu His Gln Met Thr Leu Gly Arg Val Thr Gly Thr
                85                  90                  95

Gln Glu Ala Gln Glu Gly Leu Gln Gly Gln Leu Gly Ala Leu Arg Arg
            100                 105                 110

Glu Arg Asp Gln Leu Glu Thr Gln Thr Arg Asp Leu Glu Ala Ala Tyr
        115                 120                 125

Asn Asn Leu Leu Arg Asp Lys Ser Ala Leu Glu Glu Lys Arg Gln
    130                 135                 140

Leu Glu Gln Glu Asn Glu Asp Leu Ala Arg Arg Leu Glu Ser Ser Ser
145                 150                 155                 160

Glu Glu Val Thr Arg Leu Arg Arg Gly Gln Cys Pro Ser Thr Gln Tyr
                165                 170                 175

Pro Ser Gln Asp Met Leu Pro Gly Ser Arg Glu Val Ser Gln Trp Asn
            180                 185                 190

Leu Asp Thr Leu Ala Phe Gln Glu Leu Lys Ser Glu Leu Thr Glu Val
        195                 200                 205

Pro Ala Ser Gln Ile Leu Lys Glu Asn Pro Ser Gly Arg Pro Arg Ser
    210                 215                 220

-continued

Lys Glu Gly Asp Lys Gly Cys Gly Ala Leu Val Trp Val Gly Glu Pro
225                 230                 235                 240

Val Thr Leu Arg Thr Ala Glu Thr Ile Ala Gly Lys Tyr Gly Val Trp
            245                 250                 255

Met Arg Asp Pro Lys Pro Thr His Pro Tyr Thr Gln Glu Ser Thr Trp
        260                 265                 270

Arg Ile Asp Thr Val Gly Thr Glu Ile Arg Gln Val Phe Glu Tyr Ser
    275                 280                 285

Gln Ile Ser Gln Phe Glu Gln Gly Tyr Pro Ser Lys Val His Val Leu
290                 295                 300

Pro Arg Ala Leu Glu Ser Thr Gly Ala Val Val Tyr Ala Gly Ser Leu
305                 310                 315                 320

Tyr Phe Gln Gly Ala Glu Ser Arg Thr Val Val Arg Tyr Glu Leu Asp
            325                 330                 335

Thr Glu Thr Val Lys Ala Glu Lys Glu Ile Pro Gly Ala Gly Tyr His
        340                 345                 350

Gly His Phe Pro Tyr Ala Trp Gly Gly Tyr Thr Asp Ile Asp Leu Ala
    355                 360                 365

Val Asp Glu Ser Gly Leu Trp Val Ile Tyr Ser Thr Glu Glu Ala Lys
370                 375                 380

Gly Ala Ile Val Leu Ser Lys Leu Asn Pro Ala Asn Leu Glu Leu Glu
385                 390                 395                 400

Arg Thr Trp Glu Thr Asn Ile Arg Lys Gln Ser Val Ala Asn Ala Phe
            405                 410                 415

Val Ile Cys Gly Ile Leu Tyr Thr Val Ser Ser Tyr Ser Ser Ala His
        420                 425                 430

Ala Thr Val Asn Phe Ala Tyr Asp Thr Lys Thr Gly Thr Ser Lys Thr
    435                 440                 445

Leu Thr Ile Pro Phe Thr Asn Arg Tyr Lys Tyr Ser Ser Met Ile Asp
450                 455                 460

Tyr Asn Pro Leu Glu Arg Lys Leu Phe Ala Trp Asp Asn Phe Asn Met
465                 470                 475                 480

Val Thr Tyr Asp Ile Lys Leu Leu Glu Met
            485                 490

<210> SEQ ID NO 5
<211> LENGTH: 194
<212> TYPE: PRT
<213> ORGANISM: Mus musculus

<400> SEQUENCE: 5

Arg Thr Ala Gln Phe Arg Lys Ala Asn Asp Arg Ser Gly Arg Cys Gln
1               5                   10                  15

Tyr Thr Phe Thr Val Ala Ser Pro Asn Glu Ser Ser Cys Pro Arg Glu
            20                  25                  30

Asp Gln Ala Met Ser Ala Ile Gln Asp Leu Gln Arg Asp Ser Ser Ile
        35                  40                  45

Gln His Ala Asp Leu Glu Ser Thr Lys Ala Arg Val Arg Ser Leu Glu
    50                  55                  60

Ser Leu Leu His Gln Met Thr Leu Gly Arg Val Thr Gly Thr Gln Glu
65                  70                  75                  80

Ala Gln Glu Gly Leu Gln Gly Gln Leu Gly Ala Leu Arg Arg Glu Arg
            85                  90                  95

Asp Gln Leu Glu Thr Gln Thr Arg Asp Leu Glu Ala Ala Tyr Asn Asn
        100                 105                 110

```
Leu Leu Arg Asp Lys Ser Ala Leu Glu Glu Lys Arg Gln Leu Glu
            115                 120                 125

Gln Glu Asn Glu Asp Leu Ala Arg Arg Leu Glu Ser Ser Glu Glu
        130                 135                 140

Val Thr Arg Leu Arg Arg Gly Gln Cys Pro Ser Thr Gln Tyr Pro Ser
145                 150                 155                 160

Gln Asp Met Leu Pro Gly Ser Arg Glu Val Ser Gln Trp Asn Leu Asp
                165                 170                 175

Thr Leu Ala Phe Gln Glu Leu Lys Ser Glu Leu Thr Glu Val Pro Ala
                180                 185                 190

Ser Gln

<210> SEQ ID NO 6
<211> LENGTH: 102
<212> TYPE: PRT
<213> ORGANISM: Mus musculus

<400> SEQUENCE: 6

Ala Asp Leu Glu Ser Thr Lys Ala Arg Val Arg Ser Leu Glu Ser Leu
1               5                   10                  15

Leu His Gln Met Thr Leu Gly Arg Val Thr Gly Thr Gln Glu Ala Gln
                20                  25                  30

Glu Gly Leu Gln Gly Gln Leu Gly Ala Leu Arg Arg Gly Arg Asp Gln
            35                  40                  45

Leu Glu Thr Gln Thr Arg Asp Leu Glu Ala Ala Tyr Asn Asn Leu Leu
        50                  55                  60

Arg Asp Lys Ser Ala Leu Glu Glu Lys Arg Gln Leu Gln Glu
65                  70                  75                  80

Asn Glu Asp Leu Ala Arg Arg Leu Glu Ser Ser Glu Glu Val Thr
                85                  90                  95

Arg Leu Arg Arg Gly Gln
            100

<210> SEQ ID NO 7
<211> LENGTH: 108
<212> TYPE: PRT
<213> ORGANISM: Artificial Sequence
<220> FEATURE:
<223> OTHER INFORMATION: Light chain variable region of monoclonal
      antibody 2A4

<400> SEQUENCE: 7

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Glu Tyr Ser Cys Gln Gln Tyr Asn Ser Tyr Pro Tyr
                85                  90                  95

Thr Phe Gly Gly Gly Thr Lys Leu Glu Ile Lys Arg
            100                 105
```

```
<210> SEQ ID NO 8
<211> LENGTH: 112
<212> TYPE: PRT
<213> ORGANISM: Artificial Sequence
<220> FEATURE:
<223> OTHER INFORMATION: Heavy chain variable region for monoclonal
      antibody 2A4

<400> SEQUENCE: 8

Glu Val Gln Leu Gln Gln Ser Gly Ala Glu Leu Met Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Pro Phe Val Tyr Trp Gly Gln Gly Thr Leu Val Thr Val Ser Ala
            100                 105                 110

<210> SEQ ID NO 9
<211> LENGTH: 11
<212> TYPE: PRT
<213> ORGANISM: Artificial Sequence
<220> FEATURE:
<223> OTHER INFORMATION: Monoclonal antibody 2A4 Light chain CDR1

<400> SEQUENCE: 9

Lys Ala Ser Gln Asn Val Gly Thr Asn Val Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Monoclonal antibody 2A4 Light chain CDR2

<400> SEQUENCE: 10

Ser Ala Ser Tyr Arg Tyr Ser
1               5

<210> SEQ ID NO 11
<211> LENGTH: 10
<212> TYPE: PRT
<213> ORGANISM: Artificial Sequence
<220> FEATURE:
<223> OTHER INFORMATION: Monoclonal antibody 2A4 Light chain CDR3

<400> SEQUENCE: 11

Gln Gln Tyr Asn Ser Tyr Pro Tyr Thr Phe
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Monoclonal antibody 2A4 Heavy chain CDR1
```

```
<400> SEQUENCE: 12

Gly Phe Asn Ile Lys Asp Tyr Tyr Met His
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Monoclonal antibody 2A4 Heavy chain CDR2

<400> SEQUENCE: 13

Trp Ile Asp Pro Glu Asn Gly Asp Thr Glu Tyr Ala Pro Lys Phe Gln
1               5                   10                  15

Gly

<210> SEQ ID NO 14
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 14

Gln Gln Tyr Met Tyr Leu Pro Ile Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 15

Gln Gln Tyr Phe Ala Leu Pro Ile Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 16

Gln Gln Tyr Asp Val Val Pro Arg Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 17

Gln Gln Tyr Ala Phe Phe Pro Leu Thr
1               5

<210> SEQ ID NO 18
<211> LENGTH: 17
```

-continued

<212> TYPE: PRT
<213> ORGANISM: Artificial Sequence
<220> FEATURE:
<223> OTHER INFORMATION: Monoclonal antibody 2A4 Heavy chain CDR2
      variant

<400> SEQUENCE: 18

Trp Ile Asp Pro Ala Asn Gly Ser Thr Tyr Tyr Ser Asp Lys Phe Gln
1               5                   10                  15
Gly

<210> SEQ ID NO 19
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 19

Gln Gln Tyr Lys Trp Leu Pro Leu Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 20

Gln Gln Tyr Asn Glu Leu Pro Ile Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 21

Gln Gln Tyr Asp Phe Phe Pro Leu Thr
1               5

<210> SEQ ID NO 22
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 22

Gln Gln Tyr Thr Phe Leu Pro Ile Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 23

```
Gln Gln Tyr Ser Ala Leu Pro Leu Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 24

Gln Gln Tyr Asp Ala Val Pro Leu Thr
1               5

<210> SEQ ID NO 25
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 25

Gln Gln Tyr Ser Val Leu Pro Ile Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 26

Gln Gln Tyr Asp Val Leu Pro Leu Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 27

Gln Gln Tyr Glu Phe Phe Pro Arg Thr
1               5

<210> SEQ ID NO 28
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 28

Gln Gln Tyr Phe Leu Leu Pro Ile Thr
1               5

<210> SEQ ID NO 29
<211> LENGTH: 9
<212> TYPE: PRT
<213> ORGANISM: Artificial Sequence
```

```
<220> FEATURE:
<223> OTHER INFORMATION: Monoclonal antibody 2A4 Light chain CDR3
      variant

<400> SEQUENCE: 29

Gln Gln Tyr Gln Glu Val Pro Arg Thr
1               5

<210> SEQ ID NO 30
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 30

Gln Gln Tyr Ala Ser Val Pro Leu Thr
1               5

<210> SEQ ID NO 31
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 31

Gln Gln Tyr Gly Tyr Leu Pro Leu Thr
1               5

<210> SEQ ID NO 32
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 32

Gln Gln Tyr Ala Phe Leu Pro Val Thr
1               5

<210> SEQ ID NO 33
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 33

Gln Gln Tyr Asp Arg Val Pro Leu Thr
1               5

<210> SEQ ID NO 34
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 34

Gln Gln Tyr Ala Phe Leu Pro Leu Thr
1               5
```

```
<210> SEQ ID NO 35
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 35

Gln Gln Tyr Arg Phe Leu Pro Ile Thr
1               5

<210> SEQ ID NO 36
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 36

Gln Gln Tyr Asn Ser Leu Pro Leu Thr
1               5

<210> SEQ ID NO 37
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 37

Gln Gln Tyr Met Tyr Leu Pro Leu Thr
1               5

<210> SEQ ID NO 38
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 38

Gln Gln Tyr Ala Ser Leu Pro Ile Thr
1               5

<210> SEQ ID NO 39
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 39

Gln Gln Tyr Asp Val Leu Pro Ile Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant
```

```
<400> SEQUENCE: 40

Gln Gln Tyr Ala Phe Leu Pro Ile Thr
1               5

<210> SEQ ID NO 41
<211> LENGTH: 9
<212> TYPE: PRT
<213> ORGANISM: Artificial Sequence
<220> FEATURE:
<223> OTHER INFORMATION: Monoclonal antibody 2A4 Light chain CDR3
      variant

<400> SEQUENCE: 41

Gln Gln Tyr Met Phe Leu Pro Leu Thr
1               5

<210> SEQ ID NO 42
<211> LENGTH: 17
<212> TYPE: PRT
<213> ORGANISM: Artificial Sequence
<220> FEATURE:
<223> OTHER INFORMATION: Monoclonal antibody 2A4 Heavy chain CDR2
      variant

<400> SEQUENCE: 42

Trp Ile Asp Pro Asp Asp Gly Ser Thr Tyr Tyr Ser Pro Asn Phe Lys
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: Monoclonal antibody 2A4 Heavy chain CDR2
      variant

<400> SEQUENCE: 43

Trp Ile Asp Pro Ser Asn Gly Asp Thr Tyr Tyr Ala His Arg Phe Gln
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: Monoclonal antibody 2A4 Heavy chain CDR2
      variant

<400> SEQUENCE: 44

Trp Ile Asp Pro Ala Asn Gly Ser Thr Tyr Tyr Ala Asp Asn Phe Lys
1               5                   10                  15

Gly

<210> SEQ ID NO 45
<211> LENGTH: 17
<212> TYPE: PRT
<213> ORGANISM: Artificial Sequence
<220> FEATURE:
<223> OTHER INFORMATION: Monoclonal antibody 2A4 Heavy chain CDR2
      variant
```

```
<400> SEQUENCE: 45

Trp Ile Asp Pro Glu Asp Gly Ser Thr Tyr Tyr Ser Asp Arg Phe Lys
1               5                   10                  15
Gly
```

ANTIBODIES THAT BIND TO NATIVELY FOLDED MYOCILIN

CROSS-REFERENCE TO RELATED APPLICATIONS

This application is a § 371 National Stage of International Patent Application No. PCT/US2019/065196, with an international filing date of Dec. 9, 2019, which International Patent Application No. PCT/US2019/065196 claims the benefit of US. Provisional Application Ser. No. 62/776,799, filed on Dec. 7, 2018, each of which is incorporated herein by reference in its entirety as if fully set forth below.

STATEMENT REGARDING FEDERALLY SPONSORED RESEARCH OR DEVELOPMENT

This invention was made with government support under R01 EY021205 awarded by the National Institutes of Health. The government has certain rights in the invention.

TECHNICAL FIELD OF THE INVENTION

This invention is generally related to antibodies and reagents for glaucoma research.

BACKGROUND OF THE INVENTION

Primary open angle glaucoma is the second leading cause of irreversible blindness worldwide. Five percent of the cases are linked to a gain of toxic function mutated form of myocilin. Gain of toxic function mutations in myocilin cause misfolding and aggregation which lead to increased intraocular pressure and damage to the eye.

Anti-myocilin antibodies are important to myocilin and glaucoma research. Steroid-induced myocilin upregulation is used to distinguish trabecular meshwork (TM) cells from other anterior eye cell types. This is important for cell line validation for research. Myocilin antibodies are also used to extract endogenous myocilin from media which allows for the co-purification and analysis of myocilin interacting proteins. Anti-myocilin antibodies are used to track the protein in a variety of human samples and animal models, as well as validate TM cell lines (Keller, et al., *Exp Eye Res,* 171:164-173 (2018)).

A recent study tested the commercial myocilin antibodies recommended by the TM research community (Keller, et al., *Exp Eye Res,* 171:164-173 (2018)) to identify the specific epitopes targeted (Patterson-Orazem, et al., *Exp Eye Res,* 173:109-112 (2018)). These antibodies recognized several epitopes across the myocilin protein, but were unable to distinguish between correctly folded and mutated misfolded forms. As noted above the mutated misfolded forms are linked to ocular disease (Patterson-Orazem, et al., *Exp Eye Res,* 173:109-112 (2018). Antibodies used to study myocilin contribute to a currently undefined functional picture. Lack of the ability to distinguish between folded and misfolded forms of myocilin limits insight gained from TM studies because myocilin is prone both to amyloid aggregation (Hill, et al., *Journal of Molecular Biology,* 426:921-935 (2014); Orwig, et al., *Journal of Molecular Biology,* 421:242-255 (2012)) and proteolysis (Sanchez-Sanchez, et al., *J Biol Chem,* 282:27810-27824 (2007); Goldwich, et al., *Invest Opthamol Vis Sci,* 44:1952-1961 (2003)). A more precise understanding of myocilin antibody targets, including conformational specificity, will aid in standardizing protocols and in turn, lead to a better understanding of eye physiology and disease.

Current treatments of glaucoma and ocular disease are based on data that lacks information about whether myocilin is properly folded or whether it is adopting a disease state in a given sample. Even without destabilizing mutations, myocilin is very sensitive to its chemical environment.

Thus, there is a need for anti-myocilin antibodies that can detect whether myocilin is properly folded.

It is an object of the invention to provide antibodies that specifically bind to correctly folded myocilin.

It is also an object of the invention to provide methods for validating cells and tissues that are frequently used in glaucoma research.

SUMMARY OF THE INVENTION

Myocilin-binding molecules, such as antibodies and antigen binding fragments thereof, fusion proteins, and other polypeptides that immunospecifically bind the coiled-coil domain of correctly-folded myocilin but do not bind to misfolded myocilin are provided. In some embodiments, the disclosed antibodies and antigen binding fragments thereof and fusion proteins are useful for the detection and extraction of natively folded (correctly folded) myocilin from a sample. In one embodiment, the antibody binds to correctly folded but not to misfolded myocilin under physiological conditions of the vitreous humor of the eye.

An exemplary antibody or antigen binding fragment that specifically binds to myocilin includes the light chain variable region having at least 80%, 85%, 90%, 95%, 96%, 97%, 98%, 99%, or 100% sequence identity to the amino acid sequence according to SEQ ID NO:7, and the heavy chain variable region having at least 80%, 85%, 90%, 95%, 96%, 97%, 98%, 99%, or 100% sequence identity to the amino acid sequence according to SEQ ID NO:8. The antibody can be detectably labeled. The antibody can be a monoclonal or polyclonal antibody, a humanized or chimeric antibody, a single chain antibody, a monovalent antibody, or a hybrid antibody.

Another embodiment provides an antibody or antigen-binding fragment thereof that specifically binds to natively folded myocilin, wherein the antibody includes (a) an HCDR1 domain having an amino acid sequence according to SEQ ID NO:12; (b) an HCDR2 domain having an amino acid sequence selected from the group consisting of SEQ ID NOs: 13, 18, and 42-45; (c) an HCDR3 domain having an amino acid sequence according to FVY; (d) an LCDR1 domain having an amino acid sequence according to SEQ ID NO:9; (e) an LCDR2 domain having an amino acid sequence according to SEQ ID NO:10; and (f) an LCDR3 domain having an amino acid sequence selected from the group consisting of SEQ ID NO: 11, 14-17 and 19-39.

Another embodiment provides a pharmaceutical composition including one or more of the disclosed antibodies or antigen binding fragments thereof and optionally a pharmaceutically acceptable excipient.

Another embodiment provides a myocilin fusion protein including the amino acid sequence of any one of SEQ ID NO:1-8 or a functional variant thereof linked to an immunoglobulin domain, wherein the fusion protein immunospecifically binds to correctly folded myocilin and does not bind to incorrectly folded myocilin.

Still another embodiment provides a method of isolating cells expressing native or correctly folded myocilin from a sample by contacting the sample with an amount of one or more of the disclosed antibodies or antigen binding fragments thereof or fusion proteins conjugated to a detectable label and subjecting the sample to cell sorting, wherein cells expressing natively folded myocilin are sorted and recovered. In one embodiment the sorting is performed by flow cytometry or immunoprecipitation. The isolated myocilin expressing cells are optionally subjected to further characterization or experiments.

Yet another embodiment provides a method of validating trabecular meshwork cell lines by contacting the cells with an amount of one or more of the disclosed antibodies or antigen binding fragments thereof conjugated to a detectable label and subjecting the cells to a detection method to detect the detectable label, wherein the detection of the label indicates the presence of human trabecular meshwork cells. The trabecular meshwork cells can be human, mouse, cat, rat, or monkey cells. The detection method can be selected from the group consisting of flow cytometry, Western blot, dot blot, or enzyme-linked immunosorbent assay (ELISA).

Another embodiment provides a kit for the validation of trabecular meshwork cell lines including one or more of the disclosed anti-myocilin antibody or antigen binding fragments thereof or fusion proteins conjugated to a detectable label and cell culture reagents all in a suitable container. The anti-myocilin antibody or antigen binding fragments thereof or fusion proteins can be provided as a lyophilized powder or a liquid in solution. The antibody detection reagents can be reagents for Western blot, dot blot, ELISA, cytometry or other antibody-based detection methods.

BRIEF DESCRIPTION OF THE DRAWINGS

FIG. 3A) and hCCLZ (human coiled-coil/leucine zipper; FIG. 3B).

FIGS. 5A-5D are tables showing modifications to 2A4 light chain variable CDR3 (FIGS. 5A and 5C) and 2A4 heavy chain variable CDR2 (FIGS. 5B and 5D). X indicates a residue which was fully randomized to all twenty amino acids; otherwise residues allowed are indicated above the WT sequence.

DETAILED DESCRIPTION OF THE INVENTION

I. Definitions

Figure 1A:
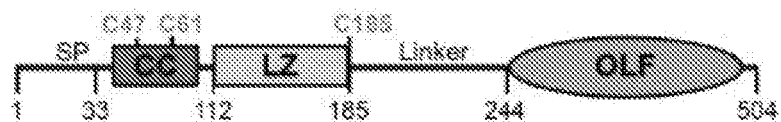
FIG. 1A is an illustration showing the gene structure depicting the domains of myocilin, including signal peptide (SP), location of key cysteine residues (C47, C61 and C185) and its coiled-coil (CC), leucine zipper (LZ) and olfactomedin (OLF) domains.

It should be appreciated that this disclosure is not limited to the compositions, methods and experimental conditions described herein, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, a molecule is said to be able to "immunospecifically bind" a second molecule if such binding exhibits the specificity and affinity of an antibody to its cognate antigen. Antibodies are said to be capable of immunospecifically binding to a target region or conformation ("epitope") of an antigen if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, BIACORE® assays, or other assays known in the art, but would not bind to a totally unrelated antigen. In some embodiments, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, MD. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079), single-chain Fvs (scFv) (see, e.g., see Pluckthun in *The Pharmacology of Monoclonal Antibodies,* vol. 113, Rosenburg and Moore eds. Springer-Verlag, New York, pp. 269-315 (1994)), single chain antibodies or nanobodies, disulfide-linked Fvs (sdFv), intrabodies, and anti-idiotypic (anti-Id) antibodies (including, e.g., anti-Id and anti-anti-Id antibodies to antibodies). In particular, such antibodies include immunoglobulin molecules of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "antigen binding fragment" of an antibody refers to one or more portions of an antibody that contain the antibody's Complementarity Determining Regions ("CDRs") and optionally the framework residues that include the antibody's "variable region" antigen recognition site, and exhibit an ability to immunospecifically bind antigen. Such fragments include Fab', $F(ab')_2$, Fv, single chain (ScFv), and mutants thereof, naturally occurring variants, and fusion proteins including the antibody's "variable region" antigen recognition site and a heterologous protein (e.g., a toxin, an antigen recognition site for a different antigen, an enzyme, a receptor or receptor ligand, etc.).

As used herein, the term "fragment" refers to a peptide or polypeptide including an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

The term "substantially," as used in the context of binding or exhibited effect, is intended to denote that the observed effect is physiologically or therapeutically relevant. Thus, for example, a molecule is able to substantially block an activity of a ligand or receptor if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

As used herein, the terms "treat," "treating," "treatment" and "therapeutic use" refer to the elimination, reduction or amelioration of one or more symptoms of a disease or disorder. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR®) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

$$100 \text{ times the fraction } W/Z,$$

where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "natively folded myocilin" refers to endogenous myocilin protein that is folded in proper way to ensure operative structure and function. "Misfolded myocilin" and "mutant myocilin" refer to myocilin that is folded in a manner that is not its native conformation, leading to improper function, as well as potential aggregate formation and damage to the eye tissue.

As used herein, a "detectable label" is a molecule or agent that is biologically or chemically attached to a protein, antibody, or amino acid to aid in the detection of said protein, antibody, or amino acid. Exemplary detectable labels include but are not limited to fluorescent, enzymatic and radioactive labels.

As used herein, "trabecular meshwork (TM) cell lines" are cells derived from trabecular meshwork tissue of the eye. TM cell lines used in ocular research are commonly derived from human, mouse, cat, monkey, or other experimental animals. The TM is located around the base of the cornea, near the ciliary body, and is responsible for draining the aqueous humor from the eye via the anterior chamber. TM cell lines must be validated because the TM is in close anatomical proximity to other regions of the eye and the TM cell culture can often become contaminated by other cell types that are inadvertently collected along with the TM. Common cell contaminants include but are not limited to scleral spur cells, keratocytes, scleral fibroblasts or Schlemm's canal cells, Validation of cell lines is achieved by detection of proteins or cell surface markers characteristic of the cell type. In the case of TM cell lines, myocilin is commonly used to detect and validate TM cells.

II. Myocilin Binding Antibodies and Fusion Proteins

Glaucoma is a group of eye conditions that damage the optic nerve, and can lead to permanent blindness. Mutations in myocilin protein have been implicated in the pathogenesis of glaucoma. However, there is limited knowledge about the function of natively folded myocilin nor is there consensus on the mutation or mutations in myocilin that lead to the detrimental aggregation and subsequent tissue damage seen in glaucoma. There is presently a lack of antibodies capable of binding to natively folded myocilin. Thus, there is a need for anti-myocilin antibodies that can detect whether myocilin is properly folded.

Antibodies and antigen binding fragments thereof and fusion proteins that immunospecifically bind the coiled-coil domain and/or leucine-zipper domain of native myocilin, and not to misfolded myocilin are provided. The disclosed antibodies and antigen-binding fragments thereof and fusion proteins are useful for the immunospecific detection and characterization of properly folded myocilin. Commercially available antibodies that are currently available for the detection and extraction of myocilin lack the conformational specificity necessary to detect correctly folded myocilin. Such antibodies include but are not limited to Abcam® ab41552 (RRID: AB_776605), Millipore® MABN866 (RRID: AB_2721107), R&D Systems® MAB3446 (RRID: AB_2148649)).

In some embodiments, disclosed antibodies, antigen binding fragments thereof, and fusion proteins target the N-terminal tetrameric coiled-coil domain and dimeric leucine-zipper domain (CCLZ region) of myocilin. In one embodiment, the disclosed antibodies and antigen binding fragments thereof and fusion proteins are recombinant, which allows for DNA sequence confirmation, unlimited production via cell culture, and facile conversion to other formats. In another embodiment, the disclosed antibodies and antigen binding fragments thereof and fusion proteins are cross-reactive, binding human and mouse myocilin (~80% sequence identity) to streamline lab reagents. In another embodiment, the disclosed antibodies are sensitive to the conformational state of myocilin, being able to differentiate between folded and unfolded myocilin.

A. Myocilin

Myocilin is secreted at relatively high levels to the outflow-regulating TM extracellular matrix within the eye (Keller, et al., *Exp Eye Res,* 171:164-173 (2018)). The TM is a specialized eye tissue involved in regulating intraocular pressure. The TM is diseased in most forms of glaucoma. At the protein level, myocilin contains multiple distinct domains: an N-terminal signal sequence for secretion, a structured coiled-coil region for multimerization, a long ~60 amino acid linker and finally, at its C-terminus, a ~250 amino acid β-propeller olfactomedin (OLF) domain. The coiled-coil region and the OLF domain are responsible for protein folding. Based on currently available data, in its native conformation, the coiled-coil region confers a Y-shaped tetrameric dimer-of-dimers architecture (Hill, et al., *Structure,* 25 (11): 1697-1707 (2017)).

Amino acid sequences for myocilin are known in the art. The amino acid sequence for human myocilin is as follows:

```
UniProt Accession No. Q99972-1, which is
incorporated by reference in its entirety.
                                         (SEQ ID NO: 1)
        10         20         30         40
MRFFCARCCS FGPEMPAVQL LLLACLVWDV GARTAQLRKA 50         60         70         80
NDQSGRCQYT FSVASPNESS CPEQSQAMSV IHNLQRDSST 90        100        110        120
QRLDLEATKA RLSSLESLLH QLTLDQAARP QETQEGLQRE 130        140        150        160
LGTLRRERDQ LETQTRELET AYSNLLRDKS VLEEEKKRLR 170        180        190        200
QENENLARRL ESSSQEVARL RRGQCPQTRD TARAVPPGSR 210        220        230        240
EVSTWNLDTL AFQELKSELT EVPASRILKE SPSGYLRSGE 250        260        270        280
GDTGCGELVW VGEPLTLRTA ETITGKYGVW MRDPKPTYPY 290        300        310        320
TQETTWRIDT VGTDVRQVFE YDLISQFMQG YPSKVHILPR 330        340        350        360
PLESTGAVVY SGSLYFQGAE SRTVIRYELN TETVKAEKEI 370        380        390        400
PGAGYHGQFP YSWGGYTDID LAVDEAGLWV IYSTDEAKGA 410        420        430        440
IVLSKLNPEN LELEQTWETN IRKQSVANAF IICGTLYTVS 450        460        470        480
SYTSADATVN FAYDTGTGIS KTLTIPFKNR YKYSSMIDYN 490        500
PLEKKLFAWD NLNMVTYDIK LSKM
```

Amino acids 1-32 of SEQ ID NO: 1 represent the signal peptide. In some embodiments, the signal peptide is post-translationally cleaved from the mature peptide.

Amino acids 33-226 of SEQ ID NO:1 represent the N-terminal domain of human myocilin. The amino acid sequence is as follows:

```
                                        (SEQ ID NO: 2)
RTAQLRKANDQSGRCQYTFSVASPNESSCPEQSQAMSVIHNLQRDSS

TQRLDLEATKARLSSLESLLHQLTLDQAARPQETQEGLQRELGTLRR

ERDQLETQTRELETAYSNLLRDKSVLEEEKKRLRQENENLARRLESS

SQEVARLRRGQCPQTRDTARAVPPGSREVSTWNLDTLAFQELKSELT

EVPASR
```

One embodiment provides an antibody or antigen binding fragment or fusion protein that immunospecifically binds to SEQ ID NO:2 or a functional fragment thereof.

Amino acids 74-184 of SEQ ID NO: 1 represent the coiled coil domain of human myocilin (hCC). The amino acid sequence is as follows:

```
                                              (SEQ ID NO: 3)
LQRDSSTQRLDLEATKARLSSLESLLHQLTLDQAARPQETQEGLQRE

LGTLRRERDQLETQTRELETAYSNLLRDKSVLEEEKKRLRQENENLA

RRLESSSQEVARLRRGQ
```

In one embodiment, the disclosed antibody or antigen binding fragment or fusion protein immunospecifically binds SEQ ID NO:3 or a functional fragment thereof.

The amino acid sequence for murine myocilin is as follows:

```
                                              (SEQ ID NO: 4)
          10          20          30          40
    MPALHLLFLA  CLVWGMGART  AQFRKANDRS  GRCQYTFTVA 50          60          70          80
    SPNESSCPRE  DQAMSAIQDL  QRDSSIQHAD  LESTKARVRS 90         100         110         120
    LESLLHQMTL  GRVTGTQEAQ  EGLQGQLGAL  RRERDQLETQ 130         140         150         160
    TRDLEAAYNN  LLRDKSALEE  EKRQLEQENE  DLARRLESSS 170         180         190         200
    EEVTRLRRGQ  CPSTQYPSQD  MLPGSREVSQ  WNLDTLAFQE 210         220         230         240
    LKSELTEVPA  SQILKENPSG  RPRSKEGDKG  CGALVWVGEP 250         260         270         280
    VTLRTAETIA  GKYGVWMRDP  KPTHPYTQES  TWRIDTVGTE 290         300         310         320
    IRQVFEYSQI  SQFEQGYPSK  VHVLPRALES  TGAVVYAGSL 330         340         350         360
    YFQGAESRTV  VRYELDTETV  KAEKEIPGAG  YHGHFPYAWG 370         380         390         400
    GYTDIDLAVD  ESGLWVIYST  EEAKGAIVLS  KLNPANLELE 410         420         430         440
    RTWETNIRKQ  SVANAFVICG  ILYTVSSYSS  AHATVNFAYD 450         460         470         480
    TKTGTSKTLT  IPFTNRYKYS  SMIDYNPLER  KLFAWDNFNM

490
    VTYDIKLLEM
```

Amino acids 1-18 of SEQ ID NO:4 represent the signal peptide. In some embodiments, the signal peptide is post-translationally cleaved from the mature peptide.

Amino acids 19-212 of SEQ ID NO:4 represent the N-terminal domain of human myocilin. The amino acid sequence is as follows:

```
                                              (SEQ ID NO: 5)
RTAQFRKANDRSGRCQYTFTVASPNESSCPREDQAMSAIQDLQRDSS

IQHADLESTKARVRSLESLLHQMTLGRVTGTQEAQEGLQGQLGALRR

ERDQLETQTRDLEAAYNNLLRDKSALEEEKRQLEQENEDLARRLESS
```

```
                                              -continued
SEEVTRLRRGQCPSTQYPSQDMLPGSREVSQWNLDTLAFQELKSELT

EVPASQ
```

One embodiment provides an antibody or antigen binding fragment or fusion protein that immunospecifically binds to SEQ ID NO:5 or a functional fragment thereof.

Amino acids 69-170 of SEQ ID NO:4 represent the coiled coil domain of human myocilin. The amino acid sequence is as follows:

```
                                              (SEQ ID NO: 6)
ADLESTKARVRSLESLLHQMTLGRVTGTQEAQEGLQGQLGALRRERD

QLETQTRDLEAAYNNLLRDKSALEEEKRQLEQENEDLARRLESSSEE

VTRLRRGQ
```

In one embodiment, the disclosed antibody or antigen binding fragment or fusion protein immunospecifically binds SEQ ID NO:6 or a functional fragment thereof.

B. Myocilin Binding Molecules

Myocilin-binding molecules, such as antibodies and antigen binding fragments thereof, fusion proteins, and other polypeptides that bind to myocilin are provided. The sequences of the heavy and light chain variable regions, and CDRs thereof, from anti-myocilin antibodies are provided below. Antibodies, antigen binding fragments and other polypeptides including one or more of the sequences below, and variants thereof are provided. For example, antibodies, antigen binding fragments, and polypeptides including one, two, or three CDRs of an anti-myocilin antibody light chain variable region and/or one, two, or three CDRs of an anti-myocilin antibody heavy chain variable region that bind to myocilin are provided. In some embodiments, the antibodies, antigen binding fragments, and polypeptides include the light chain variable region of an anti-myocilin antibody, the heavy chain variable region of an anti-myocilin, or a combination thereof, and can bind to myocilin.

1. Antibody Sequences

As described in the Examples below, mice were immunized with purified hCCLZ, a well-characterized and stable N-terminal structural domain comprising residues 69-185 and including both dimer and tetramer regions to generate a panel of antibodies. Mice were given boosters alternating between hCCLZ and mLZ (mouse leucine zipper) until sufficient immune response to both immunogens was observed in animal titers. Candidate DNA libraries were generated by extracting RNA from mouse spleens by PCR amplification of VL and VH using degenerate primers and subsequently cloning the light and heavy chains into scFv plasmid format. Thirteen candidates were identified for further characterization in scAb format. Some of the scAbs were transformed into IgG format. Monoclonal antibody 2A4 was the most promising candidate for myocilin binding.

The sequences of light and heavy chain variable regions for monoclonal antibody referred to as 2A4 are provided below.

a. Monoclonal Antibody 2A4 i. Light Chain

2A4 light chain variable region amino acid sequence is:

```
                                              (SEQ ID NO: 7)
DIVMTQSQKFMSTSVGDRVSVTCKASQNVGTNVAWYQQKPGQSPKAL

IYSASYRYSGVPDRFTGSGSGTDFTLTISNVQSEDLAEYSCQQYNSY

PYTFGGGTKLEIKR
```

-continued

2A4 Light chain CDR1 (LCDR1):
(SEQ ID NO: 9)
KASQNVGTNVA

2A4 Light chain CDR2 (LCDR2):
(SEQ ID NO: 10)
SASYRYS

2A4 Light chain CDR3 (LCDR3):
(SEQ ID NO: 11)
QQYNSYPYTF

In some embodiments, the sequence of LCDR3 is modified to improve binding to native myocilin. Exemplary modifications are shown in FIGS. 5A and 5C. Modified 2A4 light chain CDR3 can have amino acid sequences according to: SEQ ID NOs: 16-18 and 21-47.

ii. Heavy Chain

2A4 heavy chain variable region amino acid sequence is:

(SEQ ID NO: 8)
EVQLQQSGAELMRSGASVKLSCTASGFNIKDYYMHWVKQRPEQGLEW

IGWIDPENGDTEYAPKFQGKATMTADTSSNTAYLQLSSLTSEDTAVY

YCNPFVYWGQGTLVTVSA

2A4 Heavy chain CDR1 (HCDR1):
(SEQ ID NO: 12)
GFNIKDYYMH

2A4 Heavy chain CDR2 (HCDR1):
(SEQ ID NO: 13)
WIDPENGDTEYAPKFQG

2A4 Heavy chain CDR3 (HCDR3):
FVY

In some embodiments, the sequence of HCDR2 is modified to improve binding to native myocilin. Exemplary modifications are shown in FIGS. 5B and 5D. Modified 2A4 heavy chain CDR2 can have amino acid sequences according to: SEQ ID NOs: 48-51.

2. Anti-Myocilin Antibodies and Antigen Binding Fragments Thereof

Myocilin binding molecules, including antibodies and antigen binding fragments thereof, that bind to one or more myocilin polypeptides or fusion proteins, or fragments or variants thereof are disclosed. The myocilin binding molecules disclosed herein are typically monoclonal antibodies, or antigen binding fragments thereof, that bind to an epitope present on a myocilin polypeptide, or fragment or fusion thereof. In some embodiments the antibody binds to a conformational epitope. In some embodiments the antibody binds to a linear epitope. A linear epitope can be 4, 5, 6, 7, 8, 9, 10, 11, or more continuous amino acids in length. The epitope can include one or more non-amino acid elements, post-translation modifications, or a combination thereof. Examples of post-translational modifications include, but are not limited to glycosylation, phosphorylation, acetylation, citrullination and ubiquitination. For example, antibodies can bind an epitope that is formed at least in-part by one or more sugar groups.

The antibody or antigen binding fragment thereof can bind to an epitope that is present on an endogenous myocilin polypeptide, or a recombinant myocilin polypeptide, or a combination thereof. In some embodiments, the antibody or antigen binding fragment thereof binds to the extracellular domain, or a fragment thereof, or an epitope formed therefrom of myocilin.

The myocilin-binding molecules can include an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, at least 99%, or 100% identical to the amino acid sequence of the variable heavy chain and/or light chain of the antibody produced by the above clones, and which exhibits immunospecific binding to human myocilin.

For example, the disclosed myocilin-binding molecules can include a light chain variable region having the amino acids sequence of SEQ ID NO:7, or a variant thereof comprising at least 50%, 60%, 70%, 80%, 85%, 90%, 95%, 99%, or more sequence identity to SEQ ID NO:7, and which exhibits immunospecific binding to natively folded myocilin.

Additionally or alternatively the disclosed myocilin-binding molecules can include a heavy chain variable region having the amino acids sequence of SEQ ID NO:8, or a variant thereof comprising at least 50%, 60%, 70%, 80%, 85%, 90%, 95%, 99%, or more sequence identity to SEQ ID NO:8, and which exhibits immunospecific binding to natively folded myocilin.

The myocilin-binding molecule can be an immunoglobulin molecule (e.g., an antibody, diabody, fusion protein, etc.) that includes one, two or three light chain CDRs and one, two or three heavy chain CDRs (e.g., in some embodiments, three light chain CDRs and three heavy chain CDRs), wherein the light chain CDRs include: SEQ ID NOs: 9-11, or SEQ ID NOs: 16-18 and 21-47; and the heavy chain CDRs include: SEQ ID NOs: 12-14, or SEQ ID NOs: 48-51.

One embodiment provides a humanized monoclonal antibody having a variable light chain amino acid sequence that is at least 45%, at least 50%, at least 55%, at least 60%, at least 65%, at least 70%, at least 75%, at least 80%, at least 85%, at least 90%, at least 95%, at least 99%, or 100% identical to the amino acid sequence selected from the group consisting of SEQ ID NO: 7 and/or a variable heavy chain amino acid sequence that is at least 45%, at least 50%, at least 55%, at least 60%, at least 65%, at least 70%, at least 75%, at least 80%, at least 85%, at least 90%, at least 95%, at least 99%, or 100% identical to the amino acid sequence selected from the group consisting of SEQ ID NO:8.

3. Antibody Compositions

The disclosed anti-myocilin antibodies or antigen binding fragments thereof include whole immunoglobulin (i.e., an intact antibody) of any class, fragments thereof, and synthetic proteins containing at least the antigen binding variable domain of an antibody. In some embodiments, the disclosed antibody contains both an antibody light chain as well as at least the variable domain of an antibody heavy chain. In other embodiments, such molecules can further include one or more of the CH1, hinge, CH2, CH3, and CH4 regions of the heavy chain (especially, the CH1 and hinge regions, or the CH1, hinge and CH2 regions, or the CH1, hinge, CH2 and CH3 regions). The antibody can be selected from any class of immunoglobulins, including IgM, IgG, IgD, IgA and IgE, and any isotype, including $IgG_1$, $IgG_2$, $IgG_3$ and $IgG_4$. In some embodiments, the constant domain is a complement fixing constant domain where it is desired that the antibody exhibit cytotoxic activity, and the class is typically $IgG_1$. In other embodiments, where such cytotoxic activity is not desirable, the constant domain can be of the $IgG_2$ or $IgG_4$ class. The antibody can include sequences from more than one class or isotype, and selecting particular constant domains to optimize desired effector functions is within the ordinary skill in the art.

The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Some embodiments provide fragments of the anti-myocilin antibodies which have bioactivity. The fragments, whether attached to other sequences or not, may include insertions, deletions, substitutions, or other selected modifications of particular regions or specific amino acids residues, provided the activity of the fragment is not significantly altered or impaired compared to the non-modified antibody or antibody fragment.

a. Chimeric and Humanized Antibodies

Another embodiment provides chimeric anti-myocilin antibodies and antigen binding fragments thereof including one or more of the disclosed sequences and functional variants thereof are also provided that bind to myocilin.

Methods for producing chimeric antibodies are known in the art. See e.g., Morrison, 1985, *Science* 229:1202; Oi et al., 1986, *BioTechniques* 4:214; Gillies et al., 1989, *J. Immunol. Methods* 125:191-202; and U.S. Pat. Nos. 6,311,415, 5,807,715, 4,816,567, and 4,816,397. Chimeric antibodies including one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, *Molecular Immunology* 28 (4/5): 489-498; Studnicka et al., 1994, *Protein Engineering* 7:805; and Roguska et al., 1994, *Proc. Natl. Acad. Sci. USA* 91:969), and chain shuffling (U.S. Pat. No. 5,565,332).

The disclosed anti-myocilin antibodies or antigen binding fragments thereof can be human or humanized antibodies, or antigen binding fragments thereof. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J (H)) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will contain at least a portion of an immunoglobulin constant region (Fc), typically that of a human immunoglobulin.

Methods for humanizing non-human antibodies are well known in the art, see, for example, European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, *Molecular Immunology* 28 (4/5): 489-498; Studnicka et al., 1994, *Protein Engineering* 7 (6): 805-814; Roguska et al., 1994, *PNAS* 91:969-973; Tan et al., 2002, *J. Immunol.* 169:1119-1125; Caldas et al., 2000, *Protein Eng.* 13:353-360; Morea et al., 2000, *Methods* 20:267-79; Baca et al., 1997, *J. Biol. Chem.* 272:10678-10684; Roguska et al., 1996, *Protein Eng.* 9:895-904; Couto et al., 1995, *Cancer Res.* 55 (23 Supp): 5973s-5977s; Couto et al., 1995, *Cancer Res.* 55:1717-22; Sandhu, 1994, *Gene* 150:409-10; Pedersen et al., 1994, *J. Mol. Biol.* 235:959-973; Jones et al., 1986, *Nature* 321:522-525; Reichmann et al., 1988, *Nature* 332:323-329; and Presta, 1992, *Curr. Op. Struct. Biol.* 2:593-596).

Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a non-human antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies can be very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, humanized antibodies can be prepared by a process of analysis of the parental sequences and various conceptual humanized products using three dimensional models of the parental and humanized sequences. Three dimensional immunoglobulin structural models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

A human, humanized or chimeric antibody derivative can include substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Such antibodies can also include at least a portion of an immunoglobulin constant region (Fc), typically that of a human immunoglobulin. The constant domains of such antibodies can be selected with respect to the proposed function of the antibody, in particular the effector function which may be required. In some embodiments, the constant domains of such antibodies are or can include human IgA, IgD, IgE, IgG or IgM domains. In a specific embodiment, human IgG constant domains, especially of the IgG1 and IgG3 isotypes are used, when the humanized antibody derivative is intended for a therapeutic use and antibody effector functions such as antibody-dependent cell-mediated cytotoxicity (ADCC) and complement-dependent cytotoxicity (CDC) activity are needed. In alternative embodiments, IgG2 and IgG4 isotypes are used when the antibody is intended for therapeutic purposes and antibody effector function is not required. Fc constant domains including one or more amino acid modifications which alter antibody effector functions such as those disclosed in U.S. Patent Application Publication Nos. 2005/0037000 and 2005/0064514.

The framework and CDR regions of a humanized antibody need not correspond precisely to the parental sequences, e.g., the donor CDR or the consensus framework can be mutagenized by substitution, insertion or deletion of at least one residue so that the CDR or framework residue at that site does not correspond to either the consensus or the donor antibody. In some embodiments, such mutations are not extensive. Usually, at least 75% of the humanized antibody residues will correspond to those of the parental framework region (FR) and CDR sequences, more often 90%, or greater than 95%. Humanized antibodies can be produced using variety of techniques known in the art, including, but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, *Molecular Immunology* 28 (4/5): 489-498; Studnicka et al., 1994, *Protein Engineering* 7 (6): 805-814; and Roguska et al., 1994, *Proc. Natl. Acad. Sci.* 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, *J. Immunol.* 169:1119-25, Caldas et al., 2000, *Protein Eng.* 13:353-60, Morea et al., 2000, *Methods* 20:267-79, Baca et al., 1997, *J. Biol. Chem.* 272:10678-84, Roguska et al., 1996, *Protein Eng.* 9:895-904, Couto et al., 1995, *Cancer Res.* 55 (23 Supp): 5973s-5977s, Couto et al., 1995, *Cancer Res.* 55:1717-22, Sandhu, 1994, *Gene* 150:409-10, Pedersen et al., 1994, *J. Mol. Biol.* 235:959-73, Jones et al., 1986, *Nature* 321:522-525, Riechmann et al., 1988, *Nature* 332: 323, and Presta, 1992, *Curr. Op. Struct. Biol.* 2:593-596.

Often, framework residues in the framework regions will be substituted with the corresponding residue from the CDR donor antibody to alter, for example improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al., 1988, *Nature* 332:323).

Human, chimeric or humanized derivatives of the disclosed murine anti-human myocilin antibodies can be used for in vivo methods in humans. Murine antibodies or antibodies of other species can be advantageously employed for many uses (for example, in vitro or in situ detection assays, acute in vivo use, etc.). Such a human or humanized antibody can include amino acid residue substitutions, deletions or additions in one or more non-human CDRs. The humanized antibody derivative can have substantially the same binding, stronger binding or weaker binding when compared to a non-derivative humanized antibody. In specific embodiments, one, two, three, four, or five amino acid residues of the CDR have been substituted, deleted or added (i.e., mutated). Completely human antibodies are particularly desirable for therapeutic treatment of human subjects.

Such human antibodies can be made by a variety of methods known in the art including phage display methods using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Such human antibodies can be produced using transgenic mice which are incapable of expressing functional endogenous immunoglobulins, but which can express human immunoglobulin genes.

For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661, 016, 5,545,806, 5,814,318, and 5,939,598, which are incorporated by reference herein in their entirety. In addition, companies can be engaged to provide human antibodies directed against a selected antigen using technology similar to that described above.

DNA sequences coding for human acceptor framework sequences include but are not limited to FR segments from the human germline VH segment VH1-18 and JH6 and the human germline VL segment VK-A26 and JK4. In a specific embodiment, one or more of the CDRs are inserted within framework regions using routine recombinant DNA techniques. The framework regions can be naturally occurring or consensus framework regions, and human framework regions (see, e.g., Chothia et al., 1998, *"Structural Determinants in the Sequences of Immunoglobulin Variable Domain,"* J. Mol. Biol. 278:457-479 for a listing of human framework regions).

b. Single-Chain Antibodies

Another embodiment provides single-chain antibodies specific to myocilin. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. These Fvs lack the constant regions (Fc) present in the heavy and light chains of the native antibody.

c. Monovalent Antibodies

In vitro methods are also suitable for preparing monovalent antibodies. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment, called the F(ab')$_2$ fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')$_2$ fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

d. Hybrid Antibodies

In another embodiment, the antibody can be a hybrid antibody. In hybrid antibodies, one heavy and light chain pair is homologous to that found in an antibody raised against one epitope, while the other heavy and light chain pair is homologous to a pair found in an antibody raised against another epitope. This results in the property of multi-functional valency, i.e., ability to bind at least two different epitopes simultaneously. Such hybrids can be formed by fusion of hybridomas producing the respective component antibodies, or by recombinant techniques. Such hybrids may, of course, also be formed using chimeric chains.

e. Conjugates or Fusions of Antibody Fragments

The targeting function of the antibody can be used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein, comprising the antibody or antibody fragment and the therapeutic agent.

Such coupling of the antibody or fragment with the therapeutic agent can be achieved by making an immunoconjugate or by making a fusion protein, or by linking the antibody or fragment to a nucleic acid such as an siRNA, comprising the antibody or antibody fragment and the therapeutic agent.

In some embodiments, the antibody is modified to alter its half-life. In some embodiments, it is desirable to increase the half-life of the antibody so that it is present in the circulation or at the site of treatment for longer periods of time. For example, it may be desirable to maintain titers of the antibody in the circulation or in the location to be treated for extended periods of time. Antibodies can be engineered with Fc variants that extend half-life, e.g., using Xtend™ antibody half-life prolongation technology (Xencor, Monrovia, CA). In other embodiments, the half-life of the anti-DNA antibody is decreased to reduce potential side effects. The conjugates disclosed can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

4. Fusion Proteins

In some embodiments, the myocilin binding molecule is an myocilin fusion protein. Fusion proteins containing myocilin polypeptides coupled to other polypeptides to form fusion proteins are provided. Myocilin fusion polypeptides can have a first fusion partner comprising all or a part of a myocilin protein fused (i) directly to a second polypeptide or, (ii) optionally, fused to a linker peptide sequence that is fused to the second polypeptide. The fusion proteins optionally contain a domain that functions to dimerize or multimerize two or more fusion proteins. In some embodiments the fusion protein is not or does not dimerize or multimerize. The peptide/polypeptide linker domain can either be a separate domain, or alternatively can be contained within one of one of the other domains (myocilin polypeptide or second polypeptide) of the fusion protein. Similarly, the domain that functions to dimerize or multimerize the fusion proteins can either be a separate domain, or alternatively can be contained within one of one of the other domains (myocilin polypeptide, second polypeptide or peptide/polypeptide linker domain) of the fusion protein. In some embodiments, the dimerization/multimerization domain and the peptide/polypeptide linker domain are the same.

Fusion proteins disclosed herein are of formula I:

$$N-R_1-R_2-R_3-C$$

wherein "N" represents the N-terminus of the fusion protein, "C" represents the C-terminus of the fusion protein, "$R_1$" is a myocilin polypeptide, "$R_2$" is an optional peptide/polypeptide linker domain, and "$R_3$" is a second polypeptide. Alternatively, $R_3$ may be the myocilin polypeptide and $R_1$ may be the second polypeptide.

The fusion proteins can be dimerized or multimerized. Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric. As discussed above, in some embodiments the fusion protein is not or does not dimerize or multimerize.

In some embodiments, the second polypeptide contains one or more domains of an immunoglobulin heavy chain constant region, for example an amino acid sequence corresponding to the hinge, $C_H2$ and/or $C_H3$ regions of a human immunoglobulin Cγ1 chain, the hinge, $C_H2$ and/or $C_H3$ regions of a murine immunoglobulin Cγ2a chain, $C_H2$ and/or $C_H3$ regions of a human immunoglobulin Cγ1, etc.

The Fc portion of the fusion protein may be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, et al., *Mol. Immun.*, 34 (6): 441-452 (1997), Swann, et al., *Cur. Opin. Immun.*, 20:493-499 (2008), and Presta, *Cur. Opin. Immun.* 20:460-470 (2008). In some embodiments the Fc region is the native IgG1, IgG2, or IgG4 Fc region. In some embodiments the Fc region is a hybrid, for example a chimeric consisting of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region may include the entire hinge region, or less than the entire hinge region.

The disclosed fusion proteins optionally contain a peptide or polypeptide linker domain that separates the myocilin polypeptide from the second polypeptide. In some embodiments, the linker domain contains the hinge region of an immunoglobulin. In a preferred embodiment, the hinge region is derived from a human immunoglobulin. Suitable human immunoglobulins that the hinge can be derived from include IgG, IgD and IgA. In a preferred embodiment, the hinge region is derived from human IgG. Amino acid sequences of immunoglobulin hinge regions and other domains are well known in the art.

5. Methods of Making

The myocilin-binding molecules can be produced by any method known in the art useful for the production of polypeptides, e.g., in vitro synthesis, recombinant DNA production, and the like. The humanized antibodies are typically produced by recombinant DNA technology. The antibodies can be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757. Techniques for the recombinant expression of immunoglobulins, including humanized immunoglobulins, can also be found, in Goeddel et al., *Gene Expression Technology Methods in Enzymology* Vol. 185 Academic Press (1991), and Borreback, *Antibody Engineering*, W. H. Freeman (1992). Additional information concerning the generation, design and expression of recombinant antibodies can be found in Mayforth, *Designing Antibodies*, Academic Press, San Diego (1993).

An exemplary process for the production of the recombinant chimeric antibodies can include the following: a) constructing, by conventional molecular biology methods, an expression vector that encodes and expresses an antibody heavy chain in which the CDRs and variable region of an anti-myocilin antibody are fused to an Fc region derived from a human immunoglobulin, thereby producing a vector for the expression of a chimeric antibody heavy chain; b) constructing, by conventional molecular biology methods, an expression vector that encodes and expresses an antibody light chain of the murine anti-human myocilin monoclonal antibody, thereby producing a vector for the expression of chimeric antibody light chain; c) transferring the expression vectors to a host cell by conventional molecular biology methods to produce a transfected host cell for the expression of chimeric antibodies; and d) culturing the transfected cell by conventional cell culture techniques so as to produce chimeric antibodies.

An exemplary process for the production of the recombinant humanized antibodies can include the following: a) constructing, by conventional molecular biology methods, an expression vector that encodes and expresses an anti-human myocilin heavy chain in which the CDRs and a minimal portion of the variable region framework that are required to retain donor antibody binding specificity are derived from the humanized variants of anti-human myocilin antibody(ies), and the remainder of the antibody is derived from a human immunoglobulin, thereby producing a vector for the expression of a humanized antibody heavy chain; b) constructing, by conventional molecular biology methods, an expression vector that encodes and expresses an antibody light chain in which the CDRs and a minimal portion of the variable region framework that are required to retain donor antibody binding specificity are derived from a non-human immunoglobulin, such as the disclosed murine anti-human myocilin antibodies, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized antibodies; and d) culturing the transfected cell by conventional cell culture techniques so as to produce humanized antibodies.

With respect to either exemplary method, host cells can be co-transfected with such expression vectors, which can contain different selectable markers but, with the exception of the heavy and light chain coding sequences, can be identical. This procedure provides for equal expression of heavy and light chain polypeptides. Alternatively, a single vector can be used which encodes both heavy and light chain polypeptides. The coding sequences for the heavy and light chains can include cDNA or genomic DNA or both. The host cell used to express the recombinant antibody can be either a bacterial cell such as *Escherichia coli*, or a eukaryotic cell (e.g., a Chinese hamster ovary (CHO) cell or a HEK-293 cell). The choice of expression vector is dependent upon the choice of host cell, and can be selected so as to have the desired expression and regulatory characteristics in the selected host cell. Other cell lines that can be used include, but are not limited to, CHO-K1, NSO, and PER.C6 (Crucell, Leiden, Netherlands).

Any of the disclosed antibodies can be used to generate anti-idiotype antibodies using techniques well known to those skilled in the art (see, e.g., Greenspan, N. S. et al. (1989) "*Idiotypes: Structure And Immunogenicity,*" FASEB J. 7:437-444; and Nisinoff, A. (1991) "*Idiotypes: Concepts And Applications,*" *J. Immunol.* 147 (8): 2429-2438).

C. Pharmaceutical Compositions

Pharmaceutical compositions including the disclosed myocilin binding molecules are provided. Pharmaceutical compositions containing the binding agent can be for administration by parenteral (intramuscular, intraperitoneal, intravenous (IV) or subcutaneous injection), routes of administration or using bioerodible inserts and can be formulated in dosage forms appropriate for each route of administration.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed myocilin binding molecules, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed myocilin binding molecules, generally dosage levels of 0.001 to 20 mg/kg of body weight daily are administered to mammals. Generally, for intravenous injection or infusion, dosage may be lower.

In certain embodiments, the myocilin binding molecule is administered locally, for example by injection directly into a site to be treated. Typically, the injection causes an increased localized concentration of the myocilin binding molecule composition which is greater than that which can be achieved by systemic administration. The myocilin binding molecule compositions can be combined with a matrix as described above to assist in creating an increased localized concentration of the polypeptide compositions by reducing the passive diffusion of the polypeptides out of the site to be treated.

1. Formulations for Parenteral Administration

In some embodiments, the disclosed myocilin binding molecules, are administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN® 20 (polysorbate-20), TWEEN® 80 (polysorbate-80)), anti-oxidants (e.g., ascorbic acid, sodium metabisulfite), and preservatives (e.g., Thimerosal, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Controlled Delivery Polymeric Matrices

The myocilin binding molecule compositions disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides or nucleic acids encoding the fusion polypeptides, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release,* 5:13-22 (1987); Mathiowitz, et al., *Reactive Polymers,* 6:275-283 (1987); and Mathiowitz, et al., *J. Appl. Polymer Sci.,* 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Methods of Use

In one embodiment, the disclosed myocilin binding antibodies and antigen binding fragments thereof and fusion proteins are useful for detecting and quantifying the presence of correctly folded myocilin (natively folded). The myocilin-directed antibodies that are currently in use in ocular research do not differentiate between the numerous disease-associated states of myocilin protein, limiting the insight that can be gleaned from the many types of experiments that employ such reagents and add knowledge to the field of ocular physiology and disease states. The disclosed antibodies are conformationally-specific to natively folded myocilin, selectively binding to identified epitopes within myocilin only when it is in its native conformation, not when it is denatured or improperly folded. The ability to detect specific disease-associated states of myocilin is important to further characterize its role in ocular physiology and disease.

A. Validating TM Cell Lines

Human tissues, cell lines derived from human and animal tissues, and animal models are commonly used in glaucoma and ocular research. It is important to validate cell lines and animal disease models so that they accurately represent the disease state which they are mimicking. In one embodiment, the disclosed antibodies and antigen binding fragments thereof can be used to validate primary human TM cells and tissues. Myocilin expression is often used to distinguish TM cells and tissues from other anterior segment regions. In one embodiment, the presence of folded myocilin with the disclosed antibodies or antigen binding fragments is used to validate TM cell culture.

The N-terminal region of myocilin confers the oligomerization state of myocilin. Endogenous myocilin has been identified in a variety of oligomerization states, ranging from dimer to tetramer and higher with unknown functional or glaucoma relevance. In one embodiment, the disclosed antibodies are used to compare these myocilin species, and see how they change with glaucoma-relevant stressors, including but not limited to myocilin mutations, steroid treatment, mechanical stress and oxidative stress.

The disclosed myocilin antibodies and antigen binding fragments are useful in protein detection techniques known in the art. Such techniques include but are not limited to Western blot, ELISA, dot blot, immunohistochemistry, and flow cytometry. In one embodiment, the disclosed antibodies are used with more than one technique to elucidate unfolded and folded myocilin. In such an embodiment, protein detection by both Western blot and dot blot indicate the present of a linear, unfolded myocilin protein, while protein detection by dot plot alone indicates the presence of a folded, native myocilin.

The disclosed antibodies and antigen binding fragments and fusion proteins can also be used to identify myocilin binding partners. The identification of myocilin binding partners will help to identify new targets for anti-glaucoma therapies. In such an embodiment, the disclosed antibodies or antigen binding fragments are used with immunoprecipitation to pull down myocilin and then identify any proteins that were bound to the myocilin.

In another embodiment, the disclosed myocilin antibodies and fusion proteins are used in combination with currently available antibodies to detect and characterize myocilin fragments in spent TM media. Immunoprecipitation with the disclosed antibodies can pull down full length myocilin, as well as fragments containing the epitope recognized by the antibody. Additional testing of the fragments could identify the state of myocilin cleavage and post-translational processing. This could help elucidate the role of proteolytic cleavage in myocilin function and even the disease states of myocilin.

B. Diagnostic Methods

In one embodiment, the disclosed antibodies and antigen binding fragments and fusion proteins are useful for the diagnosis of glaucoma in a subject. In such an embodiment, a sample from the subject is contacted with one of disclosed antibodies and the antibody is detected by Western blot, dot blot, or both. The presence of myocilin in the dot blot only is indicative of the presence of natively folded myocilin. In one embodiment, the expression pattern of natively folded myocilin can be used to determine the health status of the eye. In such an embodiment, the presence of high levels of natively folded myocilin are indicative of good eye health. In another embodiment, tracking the expression of natively folded myocilin over time can be used to track the progression of glaucoma, with an inverse relationship between native myocilin and disease state. The less native myocilin that is present, the more likely the subject is to have disease progression of glaucoma.

In another embodiment, the disclosed antibodies and fusion proteins are used in combination with currently available antibodies that detect linear myocilin. In such an embodiment, the ratio of linear to folded myocilin is used to determine the progression of glaucoma. In such an embodiment, a higher ratio of linear myocilin to natively folded myocilin is indicative of a disease state.

C. Treating Glaucoma

The CCLZ region of myocilin is involved in myocilin binding to exogenous binding partners. While the present consensus is that misfolded mutant myocilin aggregates are responsible for ocular damage, mutant myocilin interacting with non-biological binding partners could also be involved in disease pathogenesis. Without being bound by any one theory, it is believed that by binding the CCLZ region of native myocilin with the disclosed myocilin binding molecules they can block or inhibit the interaction of myocilin with other partners.

In one embodiment, a pharmaceutical composition including the disclosed myocilin binding molecules is prophylactically administered to a subject who is at risk of developing glaucoma. The disclosed myocilin binding molecules can slow down or halt the onset of disease in the subject. In another embodiment, a subject diagnosed with glaucoma is administered a pharmaceutical composition including the disclosed myocilin binding molecules to slow down or halt disease progression.

In one embodiment, a composition including a therapeutically effective amount of myocilin binding molecules is administered to the subject once daily, twice-daily, or every other day. The subject can also be administered the composition intermittently, for example, weekly, twice-weekly, every other week, or once every three weeks. In another embodiment, the subject is administered a composition including a therapeutically effective amount of myocilin binding molecules for 1, 2, 3, 4, 5, 6, 7 or more than 7 days. In another embodiment, the subject is administered a composition including a therapeutically effective amount of myocilin binding molecules for 2, 3, 4, 5, 6, 7, 8 or more than 8 weeks. In yet another embodiment, the subject is administered a composition including a therapeutically effective amount of myocilin binding molecules for 3, 4, 5, 6, 7, 8, or more than 8 months.

IV. Kit

One embodiment provides a kit for validating cells and tissues for use in glaucoma and ocular research. In one embodiment, the kit can be used to streamline and standardize validation of human trabecular meshwork cell lines across ocular research labs throughout the world. In one embodiment, the kit includes the disclosed antibodies or antigen binding fragments, cell culture reagents, and detection reagents selected depending on the type of detection application that is desired. The antibody or antigen binding fragments or fusion protein can be provided lyophilized or in solution. The lyophilized antibodies could include written instructions for reconstitution. The detection reagents could include Western blot reagents, dot blot reagents, immunohistochemistry reagents, ELISA reagents, immunoprecipitation reagents or flow cytometry reagents. In another embodiment, the kit also includes positive control samples. Also included in the kit could be materials required to perform the detection methods including but not limited to cell culture plates, ELISA plates, Western blot/dot blot membranes, or secondary antibodies for immunohistochemistry, immunoprecipitation, and flow cytometry. In another embodiment, the kit can include other myocilin antibodies, such as linear myocilin antibodies.

EXAMPLES

General Materials and Methods

Protein expression and purification: myocilin: N-terminal myocilin fragments were expressed in *E. coli* BL21-DE3-pLysS using pET-30 XaLIC (Hill, et al., *Structure*, 25:1697-1707 (2017)) or in pMAL (hNTD, comprising residues 33-226, only) (Patterson-Orazem, et al., *Exp Eye Res*, 173:109-112 (2018)) vectors. Proteins were purified as described previously (Hill, et al., *Structure*, 25:1697-1707 (2017)) by nickel affinity chromatography followed by size-exclusion on AKTA Pure™ or Purifier™ (GER). For immunization and panning, expression tags were cleaved using Factor-Xa (New England Biolabs®) and purified proteins isolated by heparin affinity and size-exclusion chromatography. Protein concentrations were determined by absorbance at 280 nm using ExPaSy-predicted extinction coefficients, as described previously (Hill, et al., *Structure*, 25:1697-1707 (2017)).

The intent was to immunize mice with hCCLZ (comprising residues 69-185) and boost with the orthologous mouse construct mCCLZ (residues 55-171). However, post immunization, it was discovered that during purification the mCCLZ construct was cleaved by Factor Xa at a fortuitous site (TLGR92) (Hill, et al., *Structure*, 25:1697-1707 (2017)). Thus, the actual immunogen used was mLZ (residues 93-171). Similar secondary sites have been reported in literature exploring Factor-Xa specificity (Furlong, et al., *Bioorg Med Chem*, 10:3637-3647 (2002); Schilling, et al., *Biol Chem*, 392:1031-1037 (2011)).

Dot blot: For dot blot characterization, clarified cell lysates were prepared by sonicating 0.2 g cell paste in 1 mL buffer (50 mM HEPES (pH 7.5), 200 mM NaCl, 10% glycerol) until clarified, then removing the insoluble fractions by centrifugation at 17,000×g (Patterson-Orazem, et al., *Exp Eye Res*, 173:109-112 (2018)). Cell lysates used for the negative control were derived from BL21-DE3 cells expressing a non-myocilin protein with both tags present in the N-terminal constructs used here. Full-length endogenous myocilin was enriched from spent hTM medium by heparin affinity, also as described previously (Patterson-Orazem, et al., *Exp Eye Res*, 173:109-112 (2018)).

Mouse Immunization & RT PCR: All protocols were approved by the University of Texas at Austin IACUC, and all mice were handled in accordance with IACUC guidelines. Three 6 week old BALB/c mice were immunized subcutaneously with 5 mg of hCCLZ using Freund's adjuvant. Four weeks later, the mice were bled through a tail vein and boosted subcutaneously with 5 mg of mLZ using incomplete Freund's adjuvant. Mice were then sacrificed and their spleens were harvested and stored in 1 mL RNAlater solution at −80° C. Blood collected was used in an ELISA to determine the serum antibody titers against hCCLZ and mLZ. Total RNA was extracted from frozen spleens with TRIzol® (Invitrogen®) and the PureLink™ RNA kit (Invitrogen®) according to the manufacturers' instructions. Concentration of RNA was determined using a NanoDrop™ 2000 (Thermo Scientific®). RNA was stored at −80° C. until further use. For first strand cDNA synthesis, a total of 500 ng of RNA was used. First strand cDNA synthesis was performed using the SuperScript™ IV Transcriptase (Invitrogen®) kit following the manufacturer's instructions. cDNA was then stored at −20° C. until further use.

Phage Display Library Construction: Phage display libraries were constructed at U. T. Austin. The cDNA was then used to generate variable heavy (VH) and variable light (VL) chain repertoires for each mouse using the primer sets and PCR conditions described previously (Krebber, et al., *J Immunol Methods*, 201:35-55 (1997)). The VH and VL fragments were then used as a template (30 ng of each) for the overlapped PCR (Krebber, et al., *J Immunol Methods*, 201:35-55 (1997)) to generate VL-linker-VH fragments (scFv). The overlapped PCR fragments (about 10 μg per mouse scFv) were gel purified using Zymoclean™ Gel DNA Recovery kit and then digested using SfiI restriction enzyme (New England BioLabs®) overnight at 50° C. About 50 μg of freshly purified pMopac24 vector was also digested overnight using SfiI at 50° C. The digests were gel purified and cleaned using Zymoclean™ Gel DNA Recovery kit. Ligation between the two fragments was performed using T4 DNA ligase (New England BioLabs®) (400-500 μL ligations per mouse) and was left at 16° C. overnight. The next morning (after 16-18 hours), the ligation was heat inactivated for 20 minutes at 65° C. and all ligations were pooled together and concentrated using n-butanol by tenfold. The concentrated ligation was then desalted using nitrocellulose membranes for two hours before electroporating in freshly prepared XL1Blue electrocompetent cells (30 to 40 electroporations). The electroporations were recovered in warm SOC medium for 1 hour before plating on medium 2×YT agar plate with 1% glucose and 100 µg/mL ampicillin plates. An aliquot was 10-fold serially diluted and plated to count library size. Plates are left overnight at room temperature and then scraped the next morning into 2×YT medium with 1% glucose. The scraped bacteria was pooled to form the master library, then frozen down in 1 mL aliquots at −80° C. at an OD600 of 5.

Phage Production, Purification, & Panning: One aliquot from the library was thawed and used to inoculate a 30 mL 2×YT culture supplemented with 1% glucose and 100 µg/mL ampicillin at a starting OD600 of 0.08-0.1. The flask labeled "input" was then grown at 37° C. shaking at 225 RPM for 2-3 hours until the OD600 was between 0.4 and 0.6. 1 mM final IPTG concentrated as well as M13KO7 helper phage at a multiplicity of 20. The flask was allowed to shake an additional 20 to 30 minutes at 37° C. and then the temperature is switched to 25° C. Three hours after adding the helper phage, the culture was supplemented with 25 µg/mL kanamycin and allowed to shake overnight at 25° C. Phage were then purified from the supernatant of the culture using ⅕th volume of precipitation solution (2.5M NaCl and 20% PEG-8000). Phage concentration was assessed using phage forming units (pfu) with serially diluted phage added to mid-log phase XL1Blue cells. These dilutions were then plated on 2×YT agar plate with 1% glucose and 100 µg/mL ampicillin.

The first round of panning was performed using mouse anti-Myc 9E10 as bait to remove any clones with possible stop codons. The subsequent rounds were panned against hCCLZ or mLZ. For panning, the protein was coated on eight ELISA plate wells (Costar®) and allowed to incubate at 2-4 ug/mL overnight at 4° C. The following day the plates were blocked using 5% milk+1×PBST for 1 hour. Another non-coated plate was blocked with 5% milk (8 wells). Once the phage was purified from the culture's supernatant, it was resuspended in a 1:1 ratio in 10% milk and then aliquoted across 8 wells of non-coated but blocked plate and allowed to incubate at room temperature on a rocker for 1 hour. This ensures that any milk binding proteins are removed and do not propagate during the panning. The milk and phage mixture is then added to the antigen bound plate and allowed to incubate for 2 hours. Finally, the wells are washed rigorously using sterile PBS plus 0.1% Tween-20 and bound phage are eluted using 0.1 M glycine at pH of 2.5, pooled, and then neutralized with 24 uLs of 2 M Tris-HCl (pH of 8.0). Half of the output phages were added to mid-log phase XL1Blue culture and incubated for 30 minutes shaking at 37° C. The input growth process was repeated for subsequent rounds of panning until a general consensus of scFv variants was reached.

Eight ELISA plate wells (®) were coated with 50 uLs of 2 µg/mL anti-Myc (9E10 from BioXCell®) monoclonal antibody, hCCLZ protein, or mLZ protein overnight at 4° C. The library is first panned against anti-Myc antibody to ensure that only full length scFvs are screened for in subsequent rounds of panning. Panning was then performed on the hCCLZ and mLZ antigen to ensure the generation of cross reactive scFv sequences. Sequence diversity was monitored throughout all the steps by colony PCR and BstNI fingerprinting as well as Sanger Sequencing.

Monoclonal phage ELISAs were performed on unique clones with interesting complementary determining regions (CDRs). Single clone cultures (2 mL) were grown up to an OD600 of 0.5 in 2×YT media supplemented with 1% glucose and 100 µg/mL ampicillin. Single cultures were then induced with 1 mM IPTG and helper phage at a multiplicity of 20 and were left shaking at 37° C. for thirty minutes before switching to room temperature shaking. After three hours of shaking at room temperature, 50 µg/mL kanamycin was added to the cultures and they were left to shake overnight. ELISA plates were coated with 2 µg/mL antigen (hCCLZ or mLZ) diluted in PBS overnight at 4° C. The next day the phage was harvested as described previously and used as a primary stain in an ELISA. Phage binding to the antigen was detected using a 1:2000 dilution of mouse anti-M13*HRP antibody in 1×PBS, 0.1% Tween-20, 5% milk.

Single chain antibodies (scAbs): To produce soluble scAbs (VL-linker-VH-human constant κ), the pMopac24 scFvs and pMopac54 vector were miniprepped and digested with SfiI (New England BioLabs®) for 3 hours at 50° C. The inserts from the digest were then ligated into digested pMopac54 vector, which includes the human constant κ sequence and a 12×his tag. The ligation was then electroporated into BL21 (DE3) competent cells (New England BioLabs®) and plated on 2×YT agar plates supplemented with 100 µg/mL ampicillin and 1% glucose. Single colonies were sequence verified and inoculated into a 3 mL culture of TB supplemented with 100 µg/mL ampicillin and 1% glucose and were allowed to shake at 37° C. until an OD600 of 5. Smaller cultures were then used to reinoculate a larger 250 mL culture of TB in 1 L flasks. Large cultures were supplemented with 1% glucose and 100 µg/mL ampicillin and were allowed to shake overnight at 37° C. and 225 rpm. The next day the large cultures are harvested by centrifugation at 5000 rpm for ten minutes. The pellets are resuspended in fresh media and returned to flasks with fresh 250 mL TB supplemented with 100 µg/mL ampicillin. They were allowed to shake one hour at 25° C. and were then induced with a final concentration of 1 mM IPTG. They were allowed to shake for an additional five hours before the cells were harvested again. Osmotic shock was performed as previously described [71]. ScAbs were then purified using IMAC resin followed by size exclusion chromatography with a Superdex® 75 column on FPLC (GE Healthcare®). Protein concentrations were measured using Nanodrop™ 2000 and purity was assessed by SDS-PAGE on a 4-20% gel (Bio-Rad®).

Immunoglobulin G (IgGs): scFvs were generated into full length chimeric human IgG1 antibodies by cloning the VH and VL domains with primers into Igκ-Abvec and IgG-Abvec vectors as described previously (Smith, et al., Nat Protoc, 4:372-384 (2009)). IgGs were produced in CHO-K1 cells using 1:1 ratio of both heavy and light chain vectors and lipofectamine 2000 (Invitrogen®). Transfection was performed following the manufacturer's protocol using DMEM supplemented with 10% low IgG FBS. Media was collected from T-150 transfections and replaced every two days over the course of an entire week. Media was then pooled and applied to a HiTrap™ protein A column (GE Healthcare®) and eluted from the column using 0.1 M glycine (pH=2.5). Purity of proteins was assessed by SDS-PAGE gels 4-20% (Bio-Rad®) and concentration was measured using Nanodrop™ 2000.

ELISA & Competition ELISA: For all proteins, ELISA was performed by coating high binding plates (Corning® 9018) with 1 µg/mL mLZ, hCCLZ, or hCC overnight in PBS at 4° C. The following day plates were blocked with PBS supplemented with 5% milk and 0.1% Tween-20 (milk solution) for one hour at room temperature. ScAbs or IgGs were then serially diluted (1:5) in milk solution to the blocked plates. Secondaries were then added at 1:1000 dilution of either goat anti-human K*HRP for scAbs or goat anti-human IgG Fc HRP for full length antibodies. ELISAs were then developed using TMB solution (Thermo Scientific Pierce®) and then quenched with 1 N HCl.

For competition ELISA, the scAbs (starting concentration of 50 µg/mL) were serially diluted in the presence of 1:1000-1:3000 dilution of scFv variant in the presence of milk solution. The phage mixture concentration remained constant across all wells. Competition of phage and scAbs was then detected using 1:2000 dilution of mouse anti M13 HRP antibody (Table 3.1, RRID: AB_673750) in milk solution. EC50s for competition were then calculated using GraphPad® Prism™ and compared to controls. Absorbance was measured using a plate reader at wavelength of 450 nm.

Dot Blots and Western Blots: Dot and western blots were conducted using protocols previously described in detail (Patterson-Orazem, et al., *Exp Eye Res*, 173:109-112 (2018)). Briefly, protein samples were immobilized on methanol-activated polyvinylidene difluoride membranes (Millipore®) by electrophoresis for Western blots and by direct deposition of 2 µL sample per dot for dot blots. Membranes were blocked overnight in 2% milk in PBS supplemented with 0.5% TWEEN-20, then probed with primary antibodies. Custom scAbs were tested at 1 µg/mL; IgGs were tested at 0.5 µg/mL to account for bivalency. Protein expression in cell lysates was confirmed using 1:1000 mouse anti-His antibody (RRID: AB_2533947). Commercial anti-LZ antibody (RRID: AB_2148649) was used as a positive control. Custom scAbs were detected with 1:2000 (whole cell lysate dot blots) or 1:5000 (all other experiments) dilution of HRP-conjugated goat anti-human K light chain secondary antibody (RRID: AB_619883). Binding of control antibodies and custom IgGs was detected using 1:2000 (whole cell lysate dot blots) or 1:5000 (all other experiments) dilution of HRP-conjugated goat anti-mouse IgG (H+L) secondary antibody (RRID: AB_2533947).

Following application of primary and secondary antibodies, membranes were treated with HyGlo™ Quick Spray (Denville Scientific®) and imaged using an Amersham™ Imager A600 (GE Healthcare®). Western and dot blot results represent at least two biological replicates per antibody tested. Heat maps were generated by measuring the intensity of the 25-fold diluted cell lysate dots using ImageJ's Gel Analyzer function (Schneider, et al., *Nat Methods*, 9:671-675 (2012)). Heat maps were generated in Origin® 2016, and represent the average of four measurements across two biological replicates.

Immunoprecipitation: Antibodies in IgG format (0.5 ng/ml) were incubated with 10 mL spent hTM medium (experiment) or 10 mL buffer control (50 mM HEPES pH 7.5, 200 mM NaCl, 10% glycerol) overnight at 4° C. on a rocker. Subsequently, Pierce™ Protein A/G Plus agarose suspension (50 µL, ThermoFisher Scientific®) was added, and samples were rocked an additional 2 hours at room temperature. Resin was pelleted by centrifugation (10 minutes at 1,000×g), washed at least 5 times with 500 uL buffer. Bound proteins were eluted by adding 50 µL 2× Laemmli buffer, incubated for 10 minutes at room temperature, followed by pelleting and removing the supernatant. Samples were supplemented to 3% v/v β-mercaptoethanol and heated 10 minutes at 95° C. prior to SDS-PAGE and Western blot analysis.

Differential Scanning Fluorimetry: Melting temperatures were determined by differential scanning fluorimetry using 5× Sypro® Orange (Invitrogen®) and 1 µM IgG in 50 mM sodium phosphate pH 7.2, 150 mM NaCl (PBS). Samples, including protein-free controls to account for background fluorescence, were prepared on ice and dispensed into 96-well optical plates (Applied Biosystems®) in triplicate, 30 µL per well. Thermal melts were performed from 25-95° C. with a 1° C. per min ramp rate using an Applied Biosystems® Step-One Plus™ RT-PCR instrument with fixed excitation wavelength (480 nm) and ROX® emission filter (610 nm). Baseline-corrected data were analyzed via Boltzmann sigmoidal regression in Origin 2016; values represent an average of triplicate samples from two separate experiments with sample standard deviation.

Example 1. Initial Evaluation of LZ-Targeting scAbs

Results

Figure 2A:
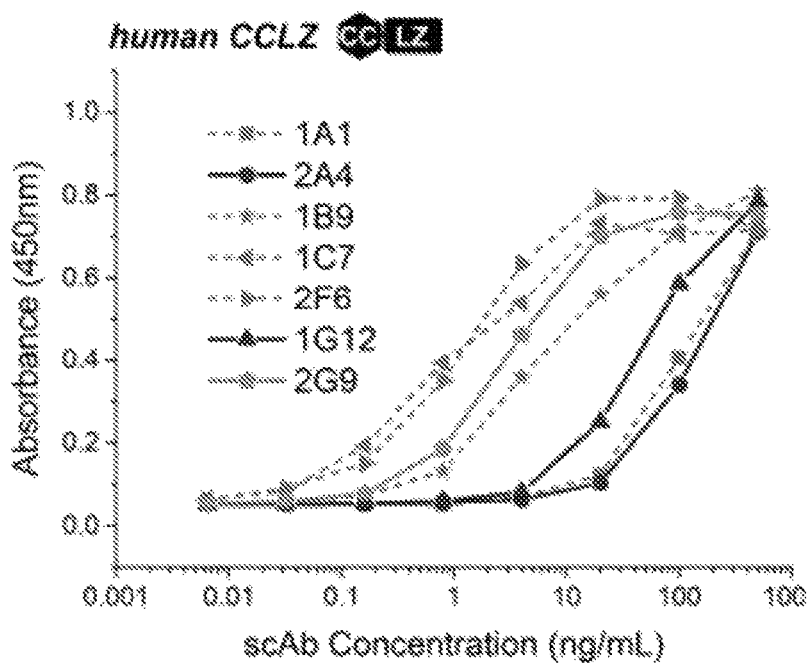
FIGS. 2A-2B are graphs showing binding affinity of candidate scAbs towards hCCLZ (FIG. 2A) and mLZ (FIG. 2B).
Figure 2B:
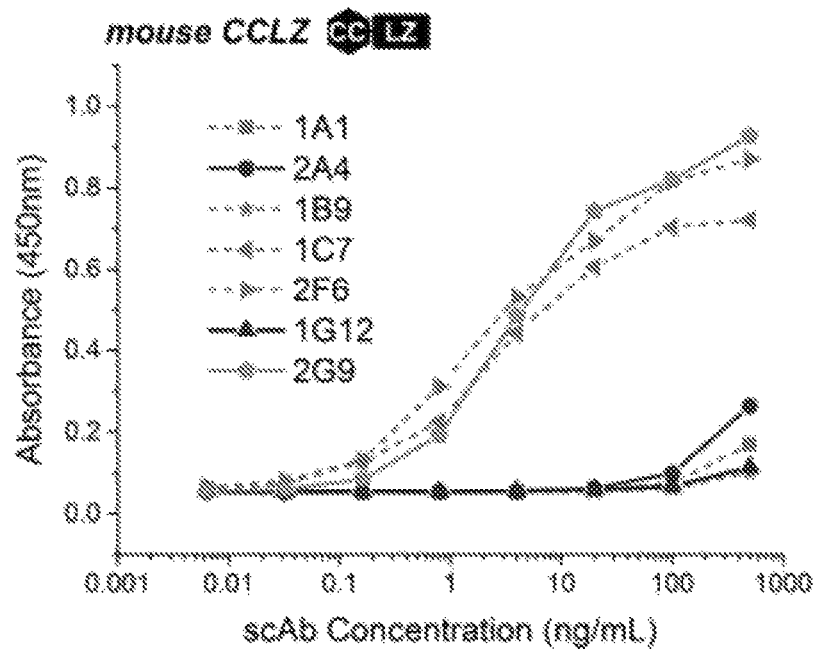
Figure 2C:
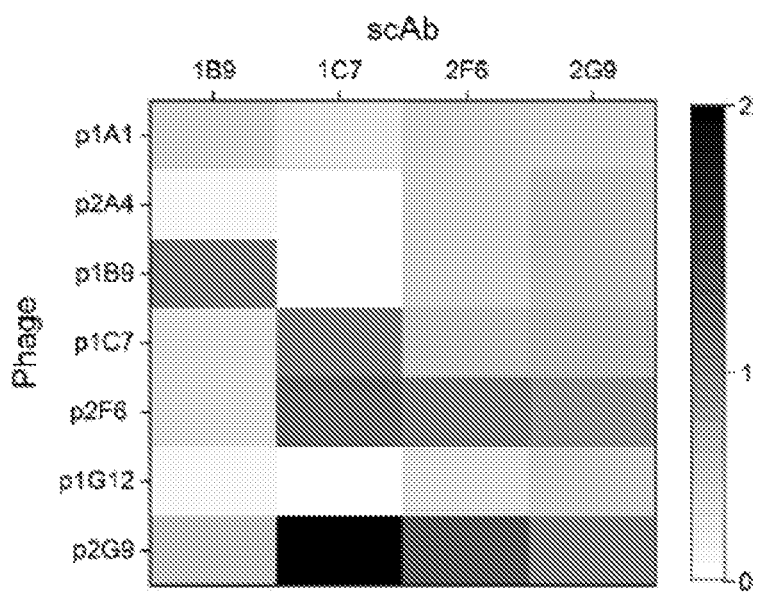
FIG. 2C is a heat map representation of competition ELISA results wherein values ≥1 indicate competing epitopes.

Candidate scAbs were produced recombinantly in a soluble form in *E. coli*, expressed and purified for further characterization. All thirteen scAbs expressed well, but six exhibited poor hCCLZ binding in follow up ELISAs (data not shown) and thus were eliminated. The remaining 7 scAbs demonstrate a range of affinities towards purified hCCLZ and mLZ in ELISA (FIGS. 2A-2B), with strongest affinity and cross-reactivity observed for 1C7, 2F6, and 2G9. Competition ELISAs reveal that 1C7, 2F6, and 2G9 target the same epitope (FIG. 2C), whereas 1B9, 1G12, 1A1, and 2A4 appear unique.

Figure 1B:
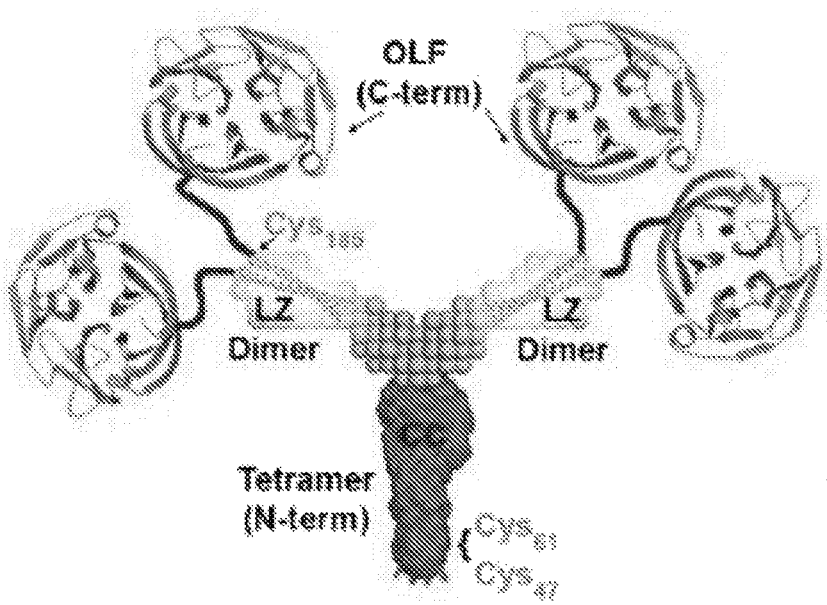
FIG. 1B is an illustration showing the myocilin quaternary structure based on solution X-ray scattering, X-ray crystallography and chemical cross-linking experiments (from Hill, et al., *Structure*, 25 (11): 1697-1707 (2017)).
Figure 2D:
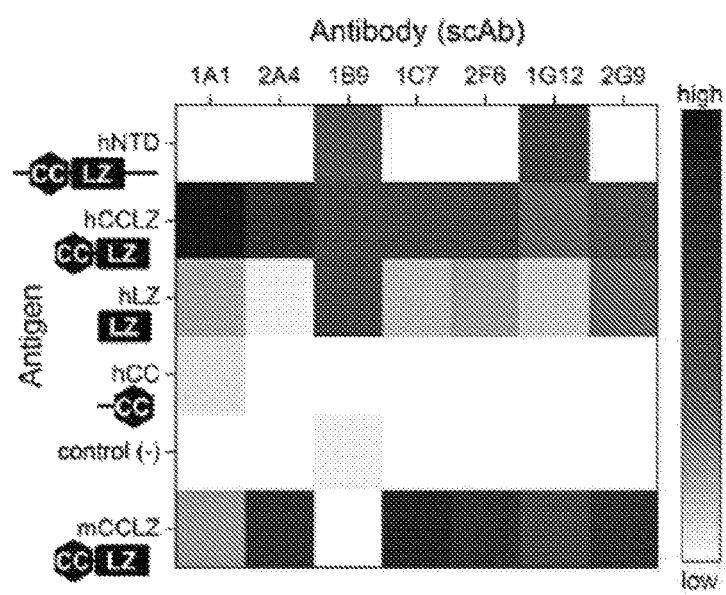
FIG. 2D is a heat map representation of scAb binding affinity in dot blots against cell lysates containing a range of N-terminal myocilin constructs or a control protein with identical tags.

Next, 1C7, 2F6, 2G9, 1B9, 1G12, 1A1, and 2A4 scAbs were tested for their ability to recognize myocilin constructs in dot blot (FIG. 2D). In this technique, the folded antigen is presented to the antibody, like in ELISA. For these experiments recognition in the context of cell lysates, not purified proteins, was tested but all were constructs previously structurally characterized (Hill, et al., *Structure*, 25:1697-1707 (2017)). All antibodies preferentially target LZ (FIG. 1B), likely due to boosting with an aberrant mouse construct (see above).

Interestingly, the majority of scAbs only weakly recognized the longer hNTD construct (residues 33-226), which includes additional linker regions before and after CCLZ, perhaps due to the previously noted conformational heterogeneity for hNTD (Hill, et al., *Structure*, 25:1697-1707 (2017)). ScAbs that initially displayed poor affinity to mLZ in ELISA (FIG. 2A) showed strong cross-reactivity to mLZ in dot blot, likely benefiting from the increased avidity afforded by the dimer-of-dimers architecture of CCLZ.

Figure 2E:
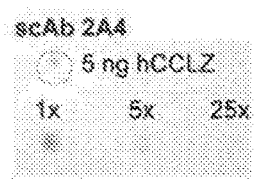
FIGS. 2E-2G are representative dot blots testing scAb binding to heparin-enriched hTM (human trabecular meshwork)-secreted myocilin.
Figure 2F:
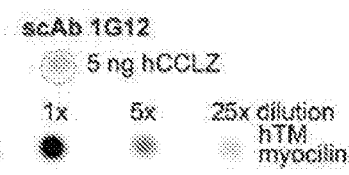
Figure 2G:
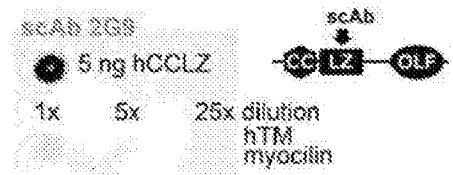

To confirm scAbs recognize full-length myocilin, dot blots with 2A4, 2G9, and 1G12 were performed using immobilized myocilin from spent media of human TM cells (FIGS. 2E-2G). Dot blots using 2A4 and 2G9 scAbs weakly, but reproducibly detected full-length myocilin. This result was surprising for 2G9, which had exhibited the strongest affinity in ELISA but appeared to very weakly recognize full-length myocilin. Conversely, dot blots with 1G12 elicited a strong signal for full-length myocilin, perhaps due to greater availability of its epitope within the protein sample or recognition of a less conformational epitope than 2A4 or 2G9 (see below).

Example 2. Evaluation of CC-Targeting scAbs

Figure 3A:
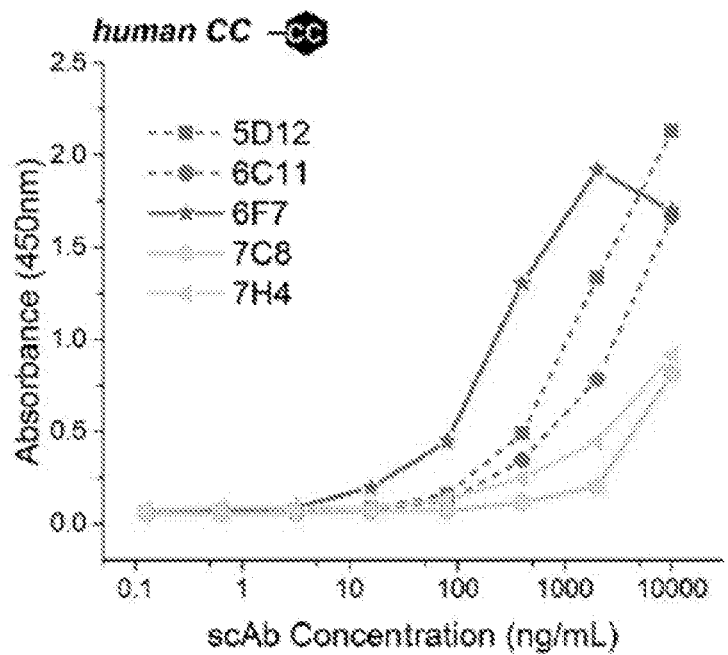
FIG. 3A-3B are graphs showing binding affinity of candidate scAbs towards hCC (human coiled-coil.
Figure 3B:
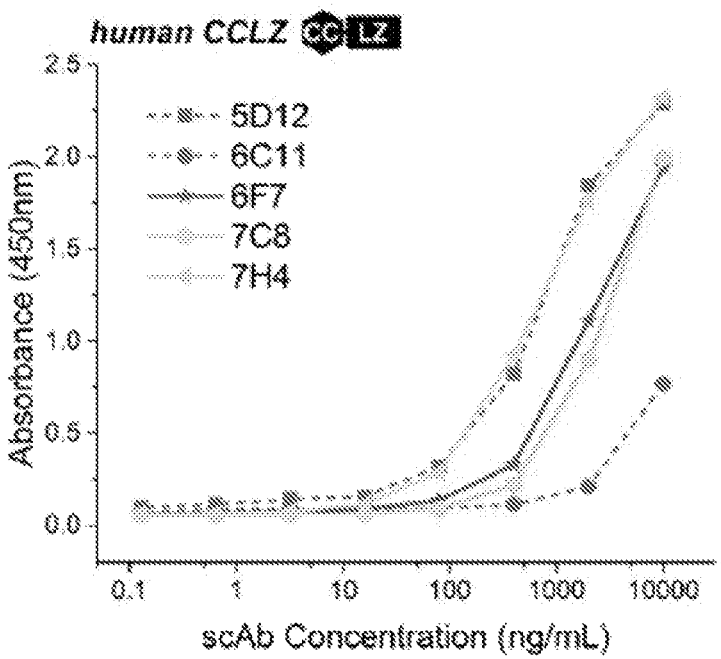
Figure 3C:
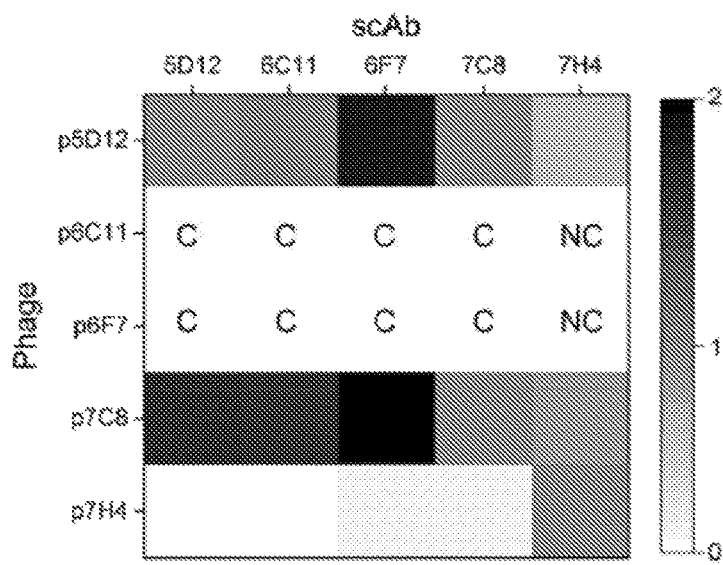
FIG. 3C is a heat map representation of competition ELISA results wherein values ≥1 indicate competing epitopes. Squares marked with letters indicate antibodies which qualitatively compete (C) or don't compete (NC) but for whom IC50 could not be calculated.

To identify antibodies targeting the CC domain (FIG. 1B), hCC (comprising residues 33-111) was panned against the scFv display library. Promising hits from phage display were expressed in *E. coli* as scAbs and analyzed as previously described for LZ-targeting scAbs. These scAbs exhibit weak affinity for hCC and hCCLZ (FIGS. 3A-3B), as ELISA was conducted at concentrations up to 10 µg/mL (FIG. 3C)

compared to 1 µg/mL for LZ-scAbs; scAb 6F7 exhibited the strongest affinity. Competition ELISA revealed that all scAbs competed for the same epitope except for 7H4 (FIG. 3C).

Figure 3D:
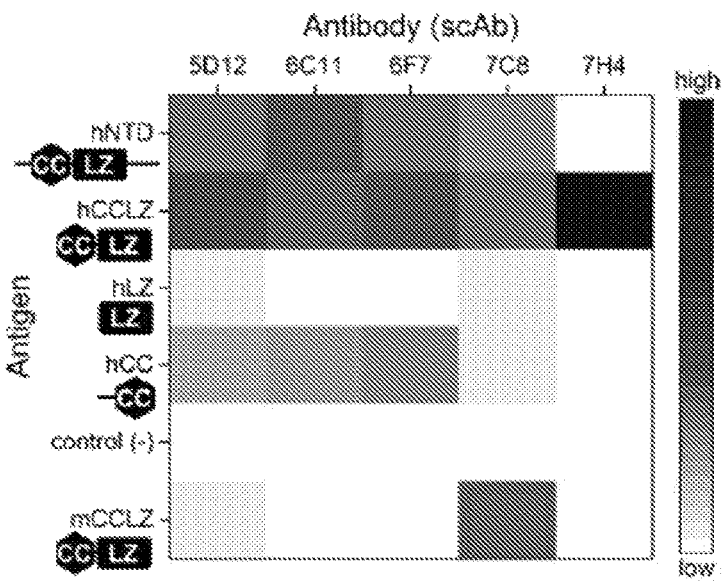
FIG. 3D is heat map representation of scAb binding affinity in dot blots against cell lysates containing a range of N-terminal myocilin constructs or a control protein with identical tags.
Figure 3E:
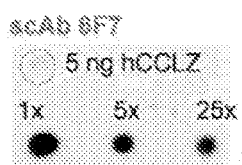
FIGS. 3E-3G are representative dot blots testing scAb binding to heparin-enriched hTM-secreted myocilin.
Figure 3F:
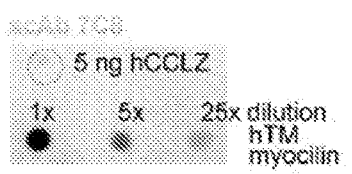
Figure 3G:

Epitope mapping of these new scAbs across the myocilin constructs in dot blot (FIG. 3D) demonstrates that 7C8 exhibits promising cross-reactivity towards mCCLZ, and 5D12 and 6C11 weakly recognize proteins within the negative control. Full-length myocilin from primary cell culture was recognized robustly by 5D12, 6C11, 6F7 and 7C8 in dot blot (FIGS. 3E-3G). Of these, three were chosen for further characterization: 6F7 (high affinity to CC without binding to negative controls), 7C8 (cross-reactivity to mouse even without selection process) and 7H4 (unique epitope).

Example 3. Conformational Specificity of CC- and LZ-Targeting IgGs

LZ-targeting (2A4, 2G9, 1G12) and CC-targeting (6F7, 7C8, 7H4) were converted next to IgG format. All but 2G9 were tested for thermal stability, with a suitable range of melting temperatures for constituent Fab domains from 64-77° C. (Ionescu, et al., *J Pharm Sci,* 97:1414-1426 (2008)). All six IgGs recognize the same epitopes as identified in scAb format but displayed apparent increased affinity, as expected for the bivalent format. Since 7H4 still bound the negative control samples, and 7C8 exhibited very weak affinity, neither was considered further.

Conformational specificity was assessed by comparing results from dot blots (FIGS. 4A-4D) and Western blots (FIG. 4E-4H), experiments were conducted in parallel with specific quantities of purified myocilin constructs. Most IgGs displayed robust affinity towards hCCLZ and hNTD in dot blots, detecting as little as 5 ng. In Western blot, where the samples are denatured, detection was weak (1G12), very weak (6F7) or not visible (2A4). 2G9 robustly recognized only hCCLZ in both Western blot and dot blot, from which we deduce that its epitope includes the C-terminal disulfide bond composed of two Cys185; this epitope is obstructed in longer constructs such as hNTD and full-length myocilin. Thus, at this point 2G9 was removed from further consideration. Weak binding of 6F7 to hNTD, but not to hCCLZ, in Western blot suggests a partial linear epitope including further N-terminal residues not present within hCCLZ.

Figure 4A:
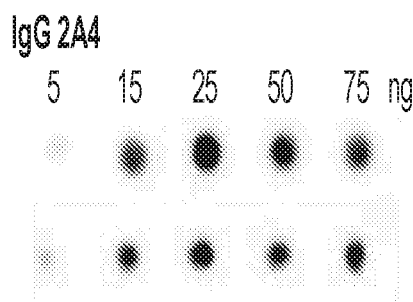
FIGS. 4A-4D are representative dot blots showing IgG binding of nanogram quantities of purified myocilin.
Figure 4B:
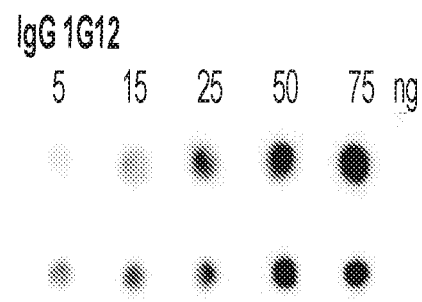
Figure 4C:
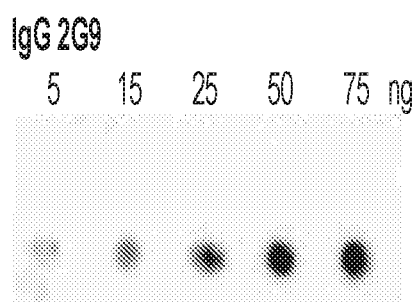
Figure 4D:
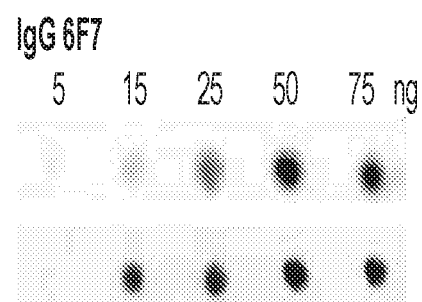
Figure 4E:
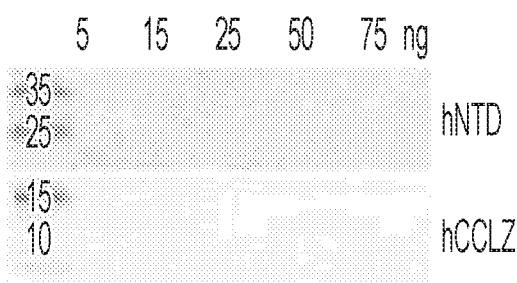
FIGS. 4E-4H are representative western blots showing IgG binding of nanogram quantities of purified myocilin.
Figure 4F:
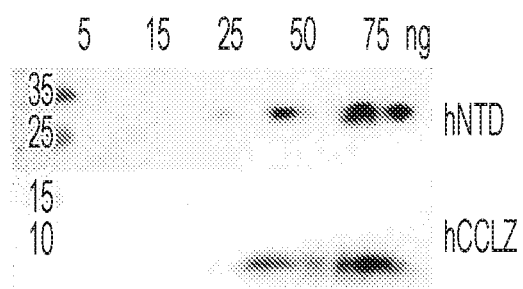
Figure 4G:
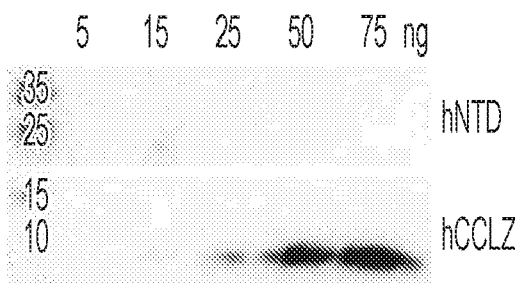
Figure 4H:
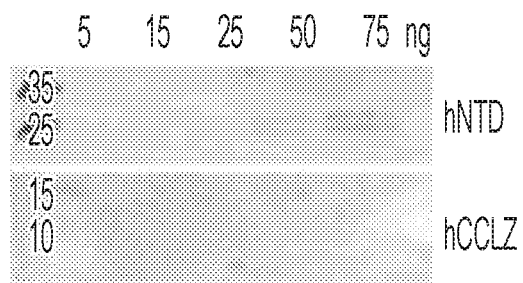
Figures 4I, 4J, 4K:
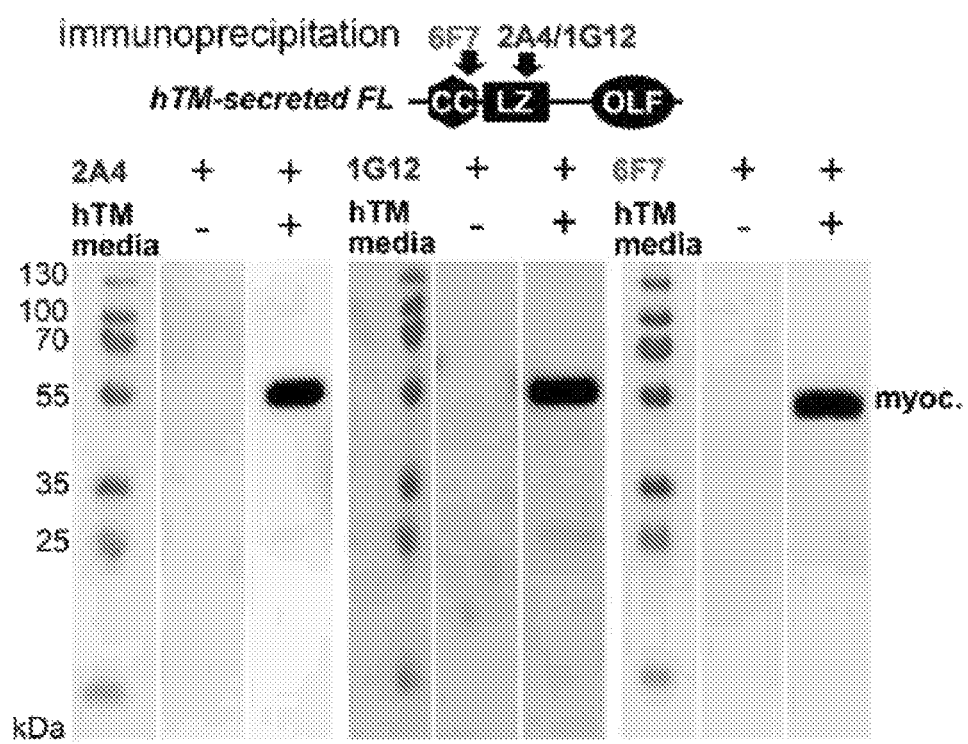
FIGS. 4I-K are IgG immunoprecipitations of hTM myocilin from spent media reveals a ~55 kDa band corresponding to full-length myocilin, detected in western blot using commercial hLZ-targeting and CC-targeting antibodies.

Finally, LZ-targeting (2A4, 1G12) and CC-targeting (6F7) IgGs were tested for their ability to purify endogenous myocilin from spent media of human TM cells. All three immunoprecipitated full-length myocilin, as well as trace amounts of an N-terminal (~25 kDa) fragment for 2A4 and 1G12 (FIGS. 4I-4K). Qualitatively, 1G12 immunoprecipitated more myocilin than did 2A4 despite similar epitope and affinity. This observation is consistent with the finding that 2A4 is selective for a folded conformation whereas 1G12 recognizes a less structural epitope, allowing it to bind additional conformers of myocilin that are apparently present in solution.

It was identified that 6F7, which targets human CC, as well as 2A4 and 1G12, which detect LZ. 6F7 and 2A4 are highly sensitive to the conformation of myocilin, as they only recognize the protein when in the folded form and not when it is denatured. 2A4 and 1G12 are both cross reactive with mouse LZ, streamlining research reagents across relevant cells, tissue samples, and glaucoma animal models (Johnson and Tomarev, *Brain Res Bull,* 81:349-358 (2010); Johnson and Tomarev, in *Animal Models of Ophthalmic Diseases,* 31-49 (2016)). It is likely that a conformational epitope conserved in mouse and human is conserved across other species used in glaucoma research, such as monkey or cat, as has been found for Ebola virus nucleoprotein (Changula et al., *Virus Res,* 176:83-90 (2013)) and pollen antigens (Westernberg, et al., *J Allergy Clin Immunol,* 138:571-578 e577 (2016)).

Through the workflow of antibody development, new insight about myocilin present in spent media from human TM cells was gleaned. First, the finding that the LZ-targeting IgGs 2A4 and 1G12 exhibit similar affinity towards recombinant myocilin yet the less-conformational 1G12 immunoprecipitates more myocilin from TM media than 2A4 indicates there is a heterogenous mixture of myocilin, including both native and non-native conformations. While the N-terminal region confers the oligomerization state of myocilin (Hill, et al., *Structure* 25, 1697-1707 (2017); (Fautsch and Johnson, *Investigative Ophthalmology & Visual Science,* 42:2324-2331 (2001)), endogenous myocilin has been identified in a variety of oligomerization states, ranging from dimer (Stamer et al., *Experimental Eye Research* 83:1386-1395 (2006)) to tetramer and higher (Fautsch, et al., *Molecular Vision* 10:417-425 (2004)), with unknown functional or glaucoma relevance. The disclosed antibodies offer the first opportunity to compare these myocilin species, and see how they change with glaucoma-relevant stressors, including but not limited to myocilin mutations (Fingert, et al., *Surv Ophthalmol* 47:547-561 (2002)), steroid treatment (Polansky et al., *Ophthalmologica,* 211:126-139 (1997)), mechanical stress (Tamm, et al., *Invest Ophthalmol Vis Sci,* 40:2577-2582 (1999)) and oxidative stress (Goyal, et al., *Curr Eye Res* 39:823-829 (2014); (Majsterek et al., *Exp Mol Pathol,* 90:231-237 (2011)). Second, immunoprecipitation with our new IgGs yielded full-length myocilin (~55 kDa) as well as a minority of truncated myocilin (~25 kDa). While myocilin cleavage has been observed in mammalian expression systems (Sanchez-Sanchez, et al., *Journal of Biological Chemistry,* 282:27810-27824 (2007); (Goldwich, et al., *Invest Ophthalmol Vis Sci,* 44:1953-1961 (2003)), this is the first observation of myocilin fragments in spent media from primary cell culture; fragments may have been detected in lysed TM cells (Ezzat et al., *Experimental Eye Research* 87:376-384 (2008)). Proteolytic cleavage for myocilin may play a functional role, as it does for olfactomedin family-members gliomedin (Y. Eshed, et al., *Journal of Cell Biology,* 177:551-562 (2007); (Maertens et al., *Journal of Biological Chemistry,* 282:10647-10659 (2007)) and latrophilin (Silva, et al., *Journal of Biological Chemistry,* 284:6495-6506 (2009)). More broadly, the availability of a myocilin epitope for detection by any given antibody might be modulated by posttranslational modification (Shepard et al., *BMC Genetics,* 4:1-10 (2003); (Gobeil et al., *Investigative Ophthalmology & Visual Science,* 45:3560-3567 (2004)) and contextual binding partners. In sum, the disclosed antibodies, in conjunction with existing antibodies targeting linear epitopes and those detecting other structural domains, will allow researchers to map myocilin with a new level of detail, in many relevant samples across vision research.

While in the foregoing specification this invention has been described in relation to certain embodiments thereof, and many details have been put forth for the purpose of illustration, it will be apparent to those skilled in the art that the invention is susceptible to additional embodiments and that certain details described herein can be varied considerably without departing from the basic principles of the invention.

All references cited herein are incorporated by reference in their entirety. The present invention may be embodied in other specific forms without departing from the spirit or

We claim:

1. An antibody or antigen-binding fragment thereof that specifically binds to natively folded myocilin but does not bind to misfolded myocilin;
    wherein the antibody comprises:
    a HCDR1 domain having the amino acid sequence according to SEQ ID NO:12;
    a HCDR2 domain having the amino acid sequence according to SEQ ID NO:13;
    a HCDR3 domain having the amino acid sequence FVY;
    a LCDR1 domain having the amino acid sequence according to SEQ ID NO:9;
    a LCDR2 domain having the amino acid sequence according to SEQ ID NO:10; and
    a LCDR3 domain having the amino acid sequence according to SEQ ID NO:11.

2. The antibody or antigen binding fragment of claim 1, wherein:
    the antibody comprises a light chain variable region (LCVR) having at least 80% sequence identity to the amino acid sequence according to SEQ ID NO: 7; and
    a heavy chain variable region (HCVR) having at least 80% sequence identity to the amino acid sequence according to SEQ ID NO: 8.

3. The antibody or antigen binding fragment of claim 1, wherein the antibody is detectably labeled.

4. The antibody or antigen binding fragment of claim 1, which comprises a HCVR that comprises the amino acid sequence set forth in SEQ ID NO: 8; and a LCVR that comprises the amino acid sequence set forth in SEQ ID NO: 7.

5. An antibody or antigen-binding fragment thereof that specifically binds to natively folded myocilin, wherein the antibody comprises:
    a HCDR1 domain having the amino acid sequence according to SEQ ID NO:12;
    a HCDR2 domain having the amino acid sequence according to SEQ ID NO: 18;
    a HCDR3 domain having the amino acid sequence FVY;
    a LCDR1 domain having the amino acid sequence according to SEQ ID NO:9;
    a LCDR2 domain having the amino acid sequence according to SEQ ID NO:10; and
    a LCDR3 domain having the amino acid sequence according to SEQ ID NO:11.

6. The antibody or antigen binding fragment of claim 5, wherein the antibody is detectably labeled.

7. A pharmaceutical composition comprising:
    the antibody or antigen binding fragment of claim 1; and
    a pharmaceutically acceptable excipient.

8. A method of isolating cells expressing native myocilin from a sample comprising:
    contacting the sample with an amount of the antibody or antigen binding fragment of claim 1; and
    subjecting the sample to cell sorting;
    wherein cells expressing natively folded myocilin are sorted and recovered.

9. The method of claim 8, wherein the sorting is performed by flow cytometry or immunoprecipitation.

10. The method of claim 8, wherein the isolated myocilin expressing cells are subjected to further characterization or experiments.

11. A method of validating trabecular meshwork cell lines comprising:
    contacting the cells with an amount of the antibody or antigen binding fragment of claim 1; and
    subjecting the cells to a detection method;
    wherein the detection of signal from a myocilin antibody indicates a presence of human trabecular meshwork cells.

12. The method of claim 11, wherein the trabecular meshwork cells are human, rat, mouse, cat, monkey, or primary trabecular meshwork cell lines from another animal.

13. The method of claim 12, wherein the detection method comprises Western blot, dot blot, or enzyme-linked immunosorbent assay (ELISA).

14. A kit for the validation of human trabecular meshwork cell lines comprising:
    the antibody or antigen binding fragments of claim 1;
    cell culture reagents; and
    antibody detection reagents.

15. The kit of claim 14, wherein the antibody or antigen binding fragment thereof are a lyophilized powder.

16. The kit of claim 14, wherein the antibody or antigen binding fragment thereof are in solution.

17. The kit of claim 14, wherein the antibody detection reagents comprise reagents for Western blot or dot blot detection.

18. The kit of claim 14, wherein the antibody detection reagents comprise reagents for ELISA detection.

* * * * *